United States Patent
Dong

(10) Patent No.: US 7,855,288 B2
(45) Date of Patent: Dec. 21, 2010

(54) PYRROLO [1,2-D] [1,2-4] TRIAZINE AS INHIBITORS OF C-JUN N TERMINAL KINASES (JNK) AND P-38 KINASES

(75) Inventor: Qing Dong, San Diego, CA (US)

(73) Assignee: Novartis AG, Basel (CH)

( * ) Notice: Subject to any disclaimer, the term of this patent is extended or adjusted under 35 U.S.C. 154(b) by 826 days.

(21) Appl. No.: 11/576,301

(22) PCT Filed: Oct. 25, 2005

(86) PCT No.: PCT/US2005/038071

§ 371 (c)(1),
(2), (4) Date: Mar. 29, 2007

(87) PCT Pub. No.: WO2006/047354

PCT Pub. Date: May 4, 2006

(65) Prior Publication Data

US 2008/0253988 A1 Oct. 16, 2008

Related U.S. Application Data

(60) Provisional application No. 60/622,519, filed on Oct. 26, 2004.

(51) Int. Cl.
*C07D 487/04* (2006.01)
*A61K 31/53* (2006.01)
*A61P 19/02* (2006.01)
*A61P 1/00* (2006.01)

(52) U.S. Cl. ................................ 544/183; 514/243
(58) Field of Classification Search ............ 544/183; 514/243

See application file for complete search history.

(56) References Cited

U.S. PATENT DOCUMENTS 5,750,522 A 5/1998 Sabb et al. .................. 514/243
2004/0082582 A1 4/2004 Dyckman et al. ........... 514/243

FOREIGN PATENT DOCUMENTS

WO 02/40486 5/2002

OTHER PUBLICATIONS

Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Cecil Textbook of Medicine, edited by Bennet, J.C., and Plum F., 20th edition, vol. 1, 1004-1010, 1996.*
Mass, R. D., Int. J. Radiation Oncology Bio. Phys. vol. 58(3): 932-940, 2004.*
Fabbro et al. Pharmacology & therapeutics 93, 79-98, 2002.*
Turner et al., Current Pharmaceutical Design. 2, 209-224, 1996.*
Sugar et al., Diagno Microbiol. Infect. Dis. 21: 129-133, 1995.*
Snyder et al., J. Med. Liban 48(4): 208-214, 2000.*

* cited by examiner

*Primary Examiner*—Venkataraman Balasubramanian
(74) *Attorney, Agent, or Firm*—Hoxie & Associates LLC

(57) ABSTRACT

A compound of formula (I): wherein the substituents are as defined in the specification as inhibitor of C-Jun N terminal Kinases (JNK) and P-38 Kinases.

11 Claims, No Drawings

PYRROLO [1,2-D] [1,2-4] TRIAZINE AS INHIBITORS OF C-JUN N TERMINAL KINASES (JNK) AND P-38 KINASES

This is the 35USC371 National Stage of International Application PCT/US2005/038071, filed Oct. 25, 2005, that claims the benefit of U.S. Provisional Application No. 60/622,519, filed Oct. 26, 2004, which, in its entirety, is herein incorporated.

FIELD

Provided herein are compounds which have cytokine inhibitory activity. The compounds in certain embodiments are pyrrolotriazine compounds for treating conditions associated with p38 kinases and/or JNK and for treating p38 kinase or JNK-associated conditions.

BACKGROUND

A large number of cytokines participate in the inflammatory response, including IL-1, IL6, IL-8 and TNF-α. Overproduction of cytokines such as IL-1 and TNF-α are implicated in a wide variety of diseases, including in flammatory bowel disease, rheumatoid arthritis, psoriasis, multiple sclerosis, endotoxin shock, osteoporosis, Alzheimer's disease, and congestive heart failure, among others [Henry et al., *Drugs Fut.*, 24:1345-1354 (1999); Salituro et al., *Curr. Med. Chem.*, 6:807-823 (1999)]. Evidence in human patients indicates that protein antagonists of cytokines are effective in treating chronic inflammatory diseases, such as, for example, monoclonal antibody to TNF-α (Remicade) [Rankin et al., *Br. J. Rheumatol.*, 34:334-342 (1995)], and soluble TNF-α receptor-Fc fusion protein (Etanercept) [Moreland et al., 25 *Ann. Intern. Med.*, 130:478-486 (1999)].

The biosynthesis of TNF-α occurs in many cell types in response to an external stimulus, such as, for example, a mitogen, an infectious organism, or trauma. Important mediators of TNF-α production are the mitogen-activated protein (MAP) kinases, including JNKs and p38 kinases. These kinases are activated in response to various stress stimuli, including but not limited to proinflammatory cytokines, endotoxin, ultraviolet light, and osmotic shock. The JNK and p38 pathways are activated by stimulation of TNF receptor family members, such as TNFR1, CD40, Herpes virus entry mediator ('HVEM')/another TNF receptor-associated protein (TRAF)-associated receptor ('ATAR'), CD95/Fas/Apo1, TRAIL/Apo2L receptors and the TNF-related activation-induced cytokine ('TRANCE') receptor, receptor activator of NF-kB ('RANK').

There are four known isoforms of p38, i.e., p38α, p38β, p38γ, and p38δ. The α and β isoforms are expressed in inflammatory cells and are key modulators of TNF-α production. Inhibiting the p38α and β enzymes in cells results in reduced levels of TNF-α expression. Also, administering inhibitors of p38α and β in animal models of inflammatory disease has proven that such inhibitors are effective in treating those diseases. Accordingly, the p38 enzymes serve an important role in inflammatory processes mediated by IL-1 and TNF-α. Compounds that reportedly inhibit p38 kinase and cytokines such as IL-1 and TNF-α for use in treating inflammatory diseases are disclosed in U.S. Pats. Nos. 6,277,989 and 6,130,235 to Scios, Inc; U.S. Pat. Nos. 6,147,080 and 5,945,418 to Vertex Pharmaceuticals Inc; U.S. Pat. Nos. 6,251,914, 5,977,103 and 5,658,903 to Smith-Kline Beecham Corp.; U.S. Pat. Nos. 5,932,576 and 6,087,496 to G. D. Searle & Co.; WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

JNK (c-Jun N-terminal kinase), also called stress activated protein kinase (SAPK), is a member of the serine/threonine MAP kinase family. MAP kinase signaling cascades are critically important in translating the signals received at the plasma membrane into changes in cellular physiology and gene expression. JNK is activated in response to a variety of stimuli, including inflammatory cytokines, growth factors and cellular stresses such as UV-light.

JNKs, along with other MAPKs, have been implicated in having a role in mediating cellular response to cancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, cancer and neurodegenerative diseases.

Three distinct genes, JNK1, JNK2, JNK3 have been identified and at least ten different splicing isoforms of JNKs exist in mammalian cells (Gupta et al., EMBO J., 15:2760-70 (1996)). Members of the JNK family are activated by proinflammatory cytokines, such as tumor necrosis factor-α (TNFα) and interleukin-1 β (IL-1β), as well as by environmental stress, including anisomycin, UV irradiation, hypoxia, and osmotic shock (Minden et al., Biochemica et Biophysica Acta, 1333:F85-F104 (1997)).

Pyrrolotriazine compounds useful as tyrosine kinase inhibitors are disclosed in U.S. patent application Ser. No. 09/573,829 filed May 18, 2000, assigned to Bristol-Myers Squibb. In addition, pyrrolotriazine kinase inhibitors are disclosed in WO 02/40486, assigned to Bristol-Myers Squibb. Other applications disclosing p38 kinase inhibitors include: WO 03/032970, WO 03/033482, WO03/032971, WO 03/032986, WO 03/032980, WO 03/032987, WO 03/033483, WO 03/033457 and WO 03/032972 are incorporated into this application. Each of the patent applications, patents, and publications referred to herein is incorporated herein by reference.

SUMMARY

Provided herein are compounds, compositions and methods of treating, preventing, or ameliorating one or more symptoms of conditions associated with p38 kinase and/or c-Jun N-terminal kinase (JNK) activity. In one embodiment, the compounds for use in the compositions and methods are pyrrolotriazines. In another embodiment, the compounds are useful as kinase inhibitors, including p38α, p38β kinases and/or c-Jun N-terminal kinases including, but not limited to, JNK1, JNK2 and JNK3.

In one embodiment, the compounds provided herein have formula I:

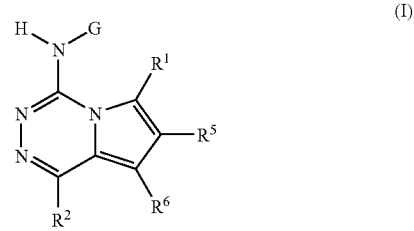

(I)

or a pharmaceutically acceptable derivative thereof, wherein G, $R^1$, $R^2$, $R^5$ and $R^6$ are selected such that the resulting compound shows p38 kinase and/or JNK activity.

Also provided are pharmaceutical compositions containing a compound of formula I as defined above in combination with a pharmaceutically acceptable carrier.

Methods of treating, preventing or ameliorating one or more symptoms of cytokine mediated disease in a mammal, by administering to a mammalian patient, in need of such treatment, a compound of formula I are provided. Diseases and disorders treated, prevented, or whose symptoms are ameliorated, include, but are not limited to, chronic inflammatory diseases, inflammatory bowel disease, rheumatoid arthritis, psoriasis, multiple sclerosis, endotoxin shock, osteoporosis, Alzheimer's disease, and congestive heart failure.

Methods of preventing or inhibiting inflammatory responses using the compounds and compositions provided herein are also provided.

Further provided are methods of inhibiting p38 kinases, including p38α and p38β kinases, and/or c-Jun N-terminal kinases, including JNK1, JKN2, and JNK3, activity using the compounds and compositions provided herein. Further provided are methods of mediating cytokine response using the compounds and compositions provided herein.

Articles of manufacture are provided containing packaging material, a compound or composition provided herein which is useful for treating, preventing, or ameliorating one or more symptoms of p38 kinase and/or JNK-mediated diseases or disorders, and a label that indicates that the compound or composition is useful for treating, preventing, or ameliorating one or more symptoms of p38 kinase and/or JNK-mediated diseases or disorders.

DETAILED DESCRIPTION

A. Definitions

Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet Reference thereto evidences the availability and public dissemination of such information.

As used herein, p38α refers to the enzyme disclosed in Han et al. (1995) *Biochim. Biophys. Acta* 1265(2-3):224-7. As used herein, p38β refers to the enzyme disclosed in Jiang et al. (1996) *J. Biol. Chem.* 271(30):17920-6. As used herein, p38γ refers to the enzyme disclosed in Li et al. (1996) *Biochem. Biophys. Res. Commun.* 228: 334-340. As used herein, p38δ refers to the enzyme disclosed in Wang et al. (1997) *J. Biol. Chem.* 272(38):23668-74.

As used herein "JNK" refers to c-Jun N-terminal kinase, also called stress activated protein kinase (SAPK). It is a member of the serine/threonine MAP kinase family. Three distinct genes, JNK1, JNK2, JNK3 have been identified and at least ten different splicing isoforms of JNKs exist in mammalian cells (Gupta et al., EMBO J., 15:2760-70 (1996)). Members of the JNK family are activated by proinflammatory cytokines, such as tumor necrosis factor-α (TNFα) and interleukin-1 β (IL-1β), as well as by environmental stress, including aniscomycin, UV irradiation, hypoxia, and osmotic shock (Minden et al., Biochemica et Biophysica Acta, 1333:F85-F104 (1997)).

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, oxalates, benzoates, salicylates, maleates, lactates, malates, tartrates, citrates, ascorbates, succinates, butyrates, valerates and fumarates. In addition, zwitterions ("inner salts") may be formed. In certain embodiments, salt forms of the compounds improve the compounds' dissolution rate and oral bioavailability. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

The term "alkyl" refers to straight or branched chain unsubstituted hydrocarbon groups of 1 to 20 carbon atoms, in one embodiment, 1 to 7 carbon atoms. The expression "lower alkyl" refers to unsubstituted alkyl groups of 1 to 4 carbon atoms. When a subscript is used with reference to an alkyl or other group, the subscript refers to the number of carbon atoms that the group may contain. The term "$C_{0-4}$alkyl" includes a bond and alkyl groups of 1 to 4 carbon atoms.

The term "cycloalkyl" refers to a saturated or partially unsaturated nonaromatic cyclic hydrocarbon ring system, preferably containing 1 to 3 rings and 3 to 7 carbons per ring which may be further fused with an unsaturated $C_3$-$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. A "substituted cycloalkyl" is substituted with one or more alkyl or substituted alkyl groups as described above, or one or more groups described above as alkyl substituents. The expression "lower cycloalkyl" refers to an unsubstituted saturated or unsaturated nonaromatic cyclic hydrocarbon ring system containing 3 to 5 carbon atoms.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkenylene" means a linear divalent hydrocarbon radical of two to six carbon atoms or a branched divalent hydrocarbon radical of three to six carbon atoms, containing at least one double bond, e.g., ethenylene, propenylene, and the like.

"Alkynyl" means a linear monovalent hydrocarbon radical of two to six carbon atoms or a branched divalent hydrocarbon radical of three to six carbon atoms, containing at least one triple bond, e.g., ethynyl, propynyl, and the like.

"Alkynylene" means a linear divalent hydrocarbon radical of two to six carbon atoms or a branched monovalent hydrocarbon radical of three to six carbon atoms, containing at least one triple bond, e.g., ethynylene, propynylene, and the like.

"Alkoxy" means a radical —OR where R is alkyl as defined above, e.g., methoxy, ethoxy, propoxy, 2-propoxy, the like.

"Acyl" means a radical —C(O)R where R is alkyl or haloalkyl e.g., acetyl, trifluoroacetyl, and the like.

"Acylamino" means a radical —NRC(O)R' where R is hydrogen or alkyl, and R' is alkyl, heteroalkyl or optionally substituted heterocyclylalkyl, e.g., acetylamino, 2-amino-2-methylpropionamide, and the like.

"Halo" means fluoro, chloro, bromo, or iodo, generally fluoro and chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Aryl" means a monovalent monocyclic or bicyclic aromatic hydrocarbon radical of 6 to 10 ring atoms e.g., phenyl, 1-naphthyl, 2-naphthyl, and the like. The aryl ring may optionally be fused to a 5-, 6- or 7-membered monocyclic saturated ring optionally containing 1 or 2 heteroatoms independently selected from oxygen, nitrogen or sulfur, the remaining ring atoms being C where one or two C atoms are optionally replaced by a carbonyl group. Representative aryl radicals with fused rings include, but are not limited to, 2,3-dihydrobenzo[1,4]dioxan, chroman, isochroman, 2,3-dihydrobenzofuran, 1,3-dihydroisobenzofuran, benzo[1,3]dioxole, 1,2,3,4-tetrahydroisoquinoline, 1,2,3,4tetrahydroquinoline, 2,3-dihydro-1H-indole, 2,3-dihydro-1H-isoindole, benzimidazol-2-one, 3H-benzoxazol-2-one, and the like.

"Heteroaryl" means a monovalent monocyclic or bicyclic aromatic radical of 5 to 10 ring atoms containing one, two, or three ring heteroatoms selected from N, O, or S, the remaining ring atoms being C. The term also includes those radicals where a heteroatom within the ring has been oxidized or quaternized, such as, for example, to form an N-oxide or a quaternary salt. Representative examples include, but are not limited to, thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, pyrazinonyl, pyridazinonyl, pyrimidinonyl, oxazolonyl, and their corresponding N-oxides, (e.g. pyridyl N-oxide, quinolinyl N-oxide), their quaternary salts and the like.

"Heterocycle" or "heterocyclyl" means a cyclic nonaromatic radical of 3 to 8 ring atoms in which one or two ring atoms are heteroatoms selected from N, O, or S(O)$_n$, (where n is an integer from 0 to 2), the remaining ring atoms being C where one or two C atoms are optionally replaced by a carbonyl group. The term also includes those radicals where a ring nitrogen atom has been oxidized or quaternized, such as, for example, to form an N-oxide or a quaternary salt. Representative examples include, but are not limited to, tetrahydropyranyl, tetrahydrofuranyl, tetrahydrothiophenyl, piperidino, morpholino, piperazino, pyrrolidino, oxiranyl, dioxane, 1,3-dioxolanyl, 2,2-dimethyl-1,3-dioxalanyl, sulfolanyl, 2-oxazolidonyl, 2-imidazolidonyl, S,S-dioxo-thiomorpholino, and the like.

"Heterocycloamino" means a saturated monovalent cyclic group of 4 to 8 ring atoms, wherein at least one ring atom is N and optionally contains one additional ring atom selected from N or O, the remaining ring atoms being C. The term includes groups such as pyrrolidino, piperidino, morpholino, piperazino and the like.

"Optionally substituted alkyl, alkenyl, alkynyl, alkoxy or cycloalkyl" means an alkyl, alkenyl, alkynyl, alkoxy or cycloalkyl group, as defined herein, which is optionally substituted independently with one, two, three or four or more substituents selected from alkyl, phenyl, benzyl, haloalkyl, heteroalkyl, halo, cyano, heterocyclyl, acyl, —OR (where R is hydrogen or alkyl), —NRR' (where R and R' are independently selected from hydrogen, acyl, or alkyl which is optionally substituted with hydroxy, alkoxy, cyano, halo or heterocyclyl), —NHCOR (where R is alkyl which is optionally substituted with hydroxy, alkoxy, cyano, halo or heterocyclyl), —NRS(O)$_n$R' (where R is hydrogen or alkyl, n is an integer from 0 to 2; and R' is hydrogen, alkyl or heteroalkyl, and is optionally substituted with hydroxy, alkoxy, cyano, halo or heterocyclyl), —NRS(O)$_n$NR'R" (where R is hydrogen or alkyl, n is an integer from 0 to 2; and R' and R" are independently hydrogen, alkyl or heteroalkyl and are optionally substituted with hydroxy, alkoxy, cyano, halo or heterocyclyl), —S(O)$_n$R (where n is an integer from 0 to 2; and R is hydrogen, alkyl or heteroalkyl and is optionally substituted with hydroxy, alkoxy, cyano, halo or heterocyclyl), —S(O)$_n$NRR' (where n is an integer from 0 to 2; and R and R' are independently hydrogen, alkyl or heteroalkyl and are optionally substituted with hydroxy, alkoxy, cyano, halo or heterocyclyl), —COOR, -(alkylene)COOR (where R is hydrogen or alkyl), —CONR'R" or -(alkylene)CONR'R" (where R' and R" are independently hydrogen or alkyl, or together form a heterocyclyl ring with the nitrogen atom to which they are attached).

"Optionally substituted aryl, heteroaryl or heterocyclyl" means an aryl, heteroaryl or heterocyclyl ring as defined above, which is optionally substituted independently with one, two, three, four or more substituents selected from alkyl, phenyl, benzyl, haloalkyl, heteroalkyl, halo, cyano, acyl, —OR (where R is hydrogen or alkyl), —NRR' (where R and R' are independently selected from hydrogen, alkyl or acyl), —NHCOR (where R is alkyl), —NRS(O)$_n$R' (where R is hydrogen or alkyl, n is an integer from 0 to 2 and R' is hydrogen, alkyl or heteroalkyl), —NRS(O)$_n$NR'R" (where R is hydrogen or alkyl, n is an integer from 0 to 2 and R' and R" are independently hydrogen, alkyl or heteroalkyl), —S(O)$_n$R (where n is an integer from 0 to 2 and R is hydrogen, alkyl or heteroalkyl), —S(O)$_n$NRR' (where n is an integer from 0 to 2 and R and R' are independently hydrogen, alkyl or heteroalkyl), —COOR, -(alkylene)COOR (where R is hydrogen or alkyl), —CONR'R" or -(alkylene)CONR'R" (where R' and R" are independently hydrogen or alkyl).

"Heteroalkyl" means an alkyl radical as defined above, carrying one, two or three substituents selected from —$NR^aR^b$, —$OR^c$ wherein $R^a$, $R^b$ and $R^c$ are independently of each other hydrogen, alkyl or acyl, or $R^a$ and $R^b$ together form heterocycloamino group. Representative examples include, but are not limited to, hydroxymethyl, acetoxymethyl, 3-hydroxypropyl, 1,2-dihydroxyethyl, 2-methoxyethyl, 2-aminoethyl, 2-dimethylaminoethyl, 2-acetylaminoethyl, 3-[pyrrolidin-1-yl]ethyl and the like.

"Heteroalkenyl" means an alkenyl radical as defined above, carrying one or two substituents selected from —$NR^aR^b$, —$OR^c$ or —$S(O)_nR^d$ wherein $R^a$, $R^b$ and $R^c$ are independently of each other hydrogen or alkyl, and $R^d$ is alkyl or —NRR' (where R and R' are independently of each other hydrogen or alkyl. Representative examples include, but are not limited to, 3-hydroxy-1-propenyl, 3-aminoprop-1-enyl, 2-aminosulfonylethenyl, 2-methylsulfonylethenyl, and the like.

"Heteroalkynyl" means an alkynyl radical as defined above, carrying one or two substituents selected —$NR^aR^b$, $OR^c$, —$S(O)_nR^d$ or —$S(O)_nNRR'$ (where R and R' are independently of each other hydrogen or alkyl) wherein $R^a$, $R^b$ and $R^c$ are independently of each other hydrogen or alkyl, and $R^d$ is alkyl and n is an integer from zero to two. Representative examples include, but are not limited to, 3-hydroxy-1-propynyl, 3-dimethylaminoprop-1-ynyl and the like.

"Heteroalkoxy" means a radical —OR where R is heteroalkyl group as defined above, e.g., 2-hydroxyethoxy, 3-hydroxypropoxy, 2,3-dihydroxypropoxy, 2-aminoethoxy, and the like.

"Heteroalkylamino" means a radical —$NR^aR^b$ where $R^a$ is hydrogen or alkyl, and $R^b$ is a heteroalkyl group as defined above, e.g., 2-hydroxyethylamino, 3-dimethylaminopropylamino, and the like.

"Optionally substituted heterocyclylalkyl" means a radical —$R^aR^b$ where $R^a$ is an alkylene group, and $R^b$ is an optionally substituted heterocyclyl group as defined above e.g., 2-(morpholin-4-yl)ethyl, 3(piperidin-1-yl)-2-methylpropyl, and the like.

"Optionally substituted heterocyclylalkenyl" means a radical —$R^aR^b$ where $R^a$ is an alkenylene group and $R^b$ is an optionally substituted heterocyclyl group as defined above e.g., 3-(morpholin-4-yl)prop-1-enyl, 3-(piperidin-1-yl)prop-1-enyl, 3-(4-methylpiperazin-1-yl)prop-1-enyl, and the like.

"Optionally substituted heterocyclylalkynyl" means a radical —$R^aR^b$ where $R^a$ is an alkynyl group and $R^b$ is an optionally substituted heterocyclyl group as defined above e.g., 3-(morpholin-4-yl)prop-1-ynyl, 3-(piperidin-1-yl)prop-1-ynyl, and the like.

"Optionally substituted heterocyclylalkoxy" means a radical —OR where R is an optionally substituted heterocyclylalkyl group as defined above, e.g., 2-(morpholin-4-yl)-ethoxy, 3-(piperazin-1-yl)propoxy, 2-[2-oxopyrrolidin-1-yl] ethoxy, and the like.

"Optionally substituted heterocyclylalkylamino" means a radical $NR^aR^b$ where $R^a$ is hydrogen or alkyl and $R^b$ is an optionally substituted heterocyclylalkyl group as defined above, e.g., 2-(pyrrolidin-2-yl)ethylamino, 3-(piperidin-1-yl) propylamino, and the like.

"Optionally substituted heteroaralkyloxy" means a radical —O—$R^a$ where $R^b$ is a heteroaralkyl radical e.g. 2-(pyridin-3-yl)ethoxy, 2-[3(2H)-pyridazon-1-yl]ethoxy and the like.

"Optional" or "optionally" means that the subsequently described event or circumstance may but need not occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the heterocyclo group is not substituted with the alkyl group.

"Amino protecting group" refers to those organic groups intended to protect nitrogen atoms against undesirable reactions during synthetic procedures e.g., benzyl, benzyloxycarbonyl (CBZ), tert-butoxycarbonyl (Boc), trifluoroacetyl, and the like.

Throughout the specification, groups and substituents thereof may be chosen by one skilled in the field to provide stable moieties and compounds. It is also understood that the chemical groups, as described herein, can be substituted or unsubstituted, branched or unbranched, as appropriate and desired.

All stereoisomers of the compounds provided herein, are contemplated, either in admixture or in pure or substantially pure form. The definition of compounds provided herein embraces all the possible stereoisomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The compounds provided herein may also have prodrug forms. Any compound that will be converted in vivo to provide the bioactive agent is a prodrug. Various forms of prodrugs are well known in the art. For examples of such prodrug derivatives, see, e.g.:

a) *Design of Prodrugs*, edited by H. Bundgaard, (Elsevier, 1985) and *Methods in Enzymology*, Vol. 42, p. 309-396, edited by K. Widder, et al. (Academic Press, 1985);

b) *A Textbook of Drug Design and Development*, edited by KrosgaardLarsen and H. Bundgaard, Chapter 5, "Design and Application of Prodrugs," by H. Bundgaard, p. 113-191 (1991); and c) H. Bundgaard, *Advanced Drug Delivery Reviews*, 8, 1-38 (1992), each of which is incorporated herein by reference.

It should further be understood that solvates (e.g., hydrates) of the compounds provided herein are also contemplated herein. Methods of solvation are generally known in the art.

As used herein, treatment means any manner in which one or more of the symptoms of a disease or disorder are ameliorated or otherwise beneficially altered. Treatment also encompasses any pharmaceutical use of the compounds and compositions herein, such as use for treating p38 kinase and/or JNK mediated diseases or disorders, or diseases or disorders in which p38 kinase activity, including p38α and p38β kinase activity, and/or JNK activity including, but not limited to, JNK1, JNK2 and JNK3 activity is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $IC_{50}$ refers to an amount, concentration or dosage of a particular test compound that achieves a 50% inhibition of a maximal response, such as modulation of p38α kinase and/or JKN activity, in an assay that measures such response.

As used herein, the term "patient" is intended to include all subjects, including mammalian species, such as humans, that are affected by mediation of p38 enzyme and/or JNK levels.

B. Compounds

In certain embodiments, the compounds provided herein are of formula:

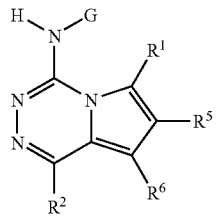

or pharmaceutically acceptable derivatives thereof, wherein:
$R^1$ is hydrogen, alkyl or halo;
$R^2$ is hydrogen or alkyl;
G is an aryl, aralkyl, cycloalkyl, heteroaryl, heteroaralkyl or a heterocyclyl ring optionally fused to a phenyl ring, and is substituted with $R^3$ and/or $R^4$;
$R^3$ is selected from the group consisting of:
(a) amino, alkylamino or dialkylamino;
(b) acylamino;
(c) optionally substituted heterocyclyl;
(d) optionally substituted aryl or heteroaryl;
(e) heteroalkyl;
(f) heteroalkenyl;
(g) heteroalkynyl;
(h) heteroalkoxy;
(i) heteroalkylamino;
(j) optionally substituted heterocyclylalkyl;
(k) optionally substituted heterocyclylalkenyl;
(l) optionally substituted heterocyclylalkynyl;
(m) optionally substituted heterocyclylalkoxy or heterocyclyloxy;
(n) optionally substituted heterocyclylalkylamino;
(o) optionally substituted heterocyclylalkylcarbonyl;
(p) heteroalkylcarbonyl;
(q) —NHSO$_2$R$^6$ where R$^6$ is alkyl, heteroalkyl or optionally substituted heterocyclylalkyl;
(r) —NHSO$_2$NR$^7$R$^8$ where R$^7$ and R$^8$ are, independently of each other, hydrogen, alkyl or heteroalkyl;
(s) —Y-(alkylene)$_{n1}$—R$^9$ where: Y is a single bond, —O—, —NH— or —S(O)$_n$— (where n and n1 are each independently an integer from 0 to 2); and R$^9$ is halo, cyano, optionally substituted aryl, optionally substituted aralkyl, optionally substituted heteroaryl, optionally substituted heterocyclyl, —COOH, —COR$^{10}$, —COOR$^{11}$, —CONR$^{12}$R$^{13}$, —SO$_2$R$^4$, —SO$_2$NR$^{15}$R$^{16}$, —NHSO$_2$R$^7$ or —NHSO$_2$NR$^{18}$R$^{19}$, where R$^{10}$ is alkyl or optionally substituted heterocycle, R$^{11}$ is alkyl, and R$^{12}$, R$^{13}$, R$^{14}$, R$^{15}$, R$^{16}$, R$^{17}$, R$^{18}$ and R$^{19}$ are, independently of each other, hydrogen, alkyl or heteroalkyl;
(t) —C(=NR$^{20}$)(NR$^{21}$R$^{22}$) where R$^{20}$, R$^{21}$ and R$^{22}$ independently represent hydrogen, alkyl or hydroxy, or R$^{20}$ and R$^{21}$ together are —(CH$_2$)$_n$— where n is 2 or 3 and R$^{22}$ is hydrogen or alkyl;

(u) —NHC(X)NR$^{23}$R$^{24}$ where X is —O— or —S—, and R$^{23}$ and R$^{24}$ are, independently of each other, hydrogen, alkyl or heteroalkyl;
(v) —CONR$^{25}$R$^{26}$ where R$^{25}$ and R$^{26}$ independently represent hydrogen, alkyl, heteroalkyl, aryl, aralkyl, cycloalkyl or optionally substituted heterocyclylalkyl, or R$^{25}$ and R$^{26}$ together with the nitrogen to which they are attached form an optionally substituted heterocyclyl ring;
(w) —S(O)$_n$R$^{27}$ where n is an integer from 0 to 2, and R$^{27}$ is alkyl, heteroalkyl, optionally substituted heterocyclylalkyl or —NR$^{28}$R$^{29}$ where R$^{28}$ and R$^{29}$ are, independently of each other, hydrogen, alkyl or heteroalkyl;
(x) cycloalkylalkyl, cycloalkylalkynyl and cycloalkylalkynyl, all optionally substituted with alkyl, halo, hydroxy or amino;
(y) arylaminoalkylene or heteroarylaminoalkylene;
(z) Z-alkylene-NR$^{30}$R$^{31}$ or Z-alkylene-OR$^{32}$ where Z is —NH—, —N(lower alkyl)- or —O—, and R$^{30}$, R$^{31}$ and R$^{32}$ are independently of each other, hydrogen, alkyl or heteroalkyl;
(aa) —OC(O)-alkylene-CO$_2$H or —OC(O)—NR'R" where R' and R" are independently hydrogen or alkyl;
(bb) heteroarylalkenylene or heteroarylalkynylene;
(cc) hydrogen;
(dd) halo;
(ee) pseudohalo;
(ff) hydroxy;
(gg) optionally substituted alkoxy;
(hh) C(L)R$^{40}$, where L is O, S or NR$^{55}$; R$^{40}$ is hydrogen, optionally substituted alkyl, optionally substituted alkenyl, optionally substituted alkynyl, optionally substituted aryl, optionally substituted heteroaryl, optionally substituted heteroarylium, optionally substituted cycloalkyl, optionally substituted heterocyclyl, C(L)R$^{56}$, halo pseudohalo, OR$^{55}$, SR$^{55}$, NR$^{57}$R$^{58}$ or SiR$^{52}$R$^{53}$R$^{54}$; where R$^{52}$, R$^{53}$ and R$^{54}$ are selected as in (i) or (ii) as follows (i) R$^{52}$, R$^{53}$ and R$^{54}$ are each independently hydrogen, alkyl, alkenyl, alkynyl, aryl, heteroaryl, heteroarylium, cycloalkyl, heterocyclyl, OR$^{55}$ or NR$^{62}$R$^{63}$; or (ii) any two of R$^{52}$, R$^{53}$ and R$^{54}$ together form alkylene, alkenylene, alkynylene, heteroalkylene; and the other is selected as in (i); R$^{55}$ is hydrogen, alkyl, alkenyl, alkynyl, aryl, heteroaryl, heteroarylium, cycloalkyl or heterocyclyl; R$^{56}$ is hydrogen, alkyl, alkenyl, alkynyl, aryl, heteroaryl, heteroarylium, cycloalkyl, heterocyclyl, OR$^{55}$ or NR$^{64}$R$^{65}$; where R$^{64}$ and R$^{65}$ are each independently hydrogen, alkyl, alkenyl, alkynyl, aryl, heteroaryl, heteroarylium, cycloalkyl, heterocyclyl, OR$^{66}$ or NR$^{62}$R$^{63}$, or R$^{64}$ and R$^{65}$ together form alkylene, alkenylene, alkynylene, heteroalkylene, where R$^{66}$ is hydrogen, alkyl, alkenyl, alkynyl, aryl, heteroaryl, heteroarylium, cycloalkyl or heterocyclyl; R$^{57}$ and R$^{58}$ are selected as in (i) or (ii) as follows (i) R$^{57}$ and R$^{58}$ are each independently hydrogen, optionally substituted alkyl, alkenyl, alkynyl, aryl, heteroaryl, heteroarylium, cycloalkyl, heterocyclyl, OR$^{55}$, NR$^{67}$R$^{68}$ or C(L)R$^{69}$, where R$^{67}$ and R$^{68}$ are each independently hydrogen, alkyl, alkenyl, alkynyl, aryl, heteroaryl, heteroarylium, cycloalkyl or heterocyclyl, or together form alkylene, alkenylene, alkynylene, heteroalkylene; and R$^{69}$ is hydrogen, alkyl, alkenyl, alkynyl, aryl, heteroaryl, heteroarylium, cycloalkyl, heterocyclyl, OR$^{70}$ or NR$^{62}$R$^{63}$, where R$^{70}$ is alkyl, alkenyl, alkynyl, aryl, heteroaryl, heteroarylium, cycloalkyl, heterocyclyl; or (ii) R$^{57}$ and R$^{58}$ together form alkylene, alkenylene, alkynylene, heteroalkylene, or alkylenoxyalkylene; R$^{62}$ and R$^{63}$ are each independently hydrogen, alkyl, alkenyl, alkynyl, aryl, heteroaryl, heteroarylium, cycloalkyl, heterocyclyl, or R$^{62}$ and R$^{63}$ together form alkylene, alkenylene, alkynylene, heteroalkylene; and (ii) optionally substituted alkyl;
$R^4$ is selected from the group consisting of:
(a) hydrogen;
(b) halo;
(c) alkyl;
(d) alkoxy; and
(e) hydroxy;
or $R^3$ and $R^4$, which substitute adjacent atoms on a ring, together form alkylenedioxy, thioalkylenoxy or alkylenedithioxy;
$R^5$ is selected from the group consisting of (a) hydrogen;
(b) halo;
(c) alkyl;
(d) haloalkyl;
(e) thioalkyl;
(f) hydroxy;
(g) amino;
(h) alkylamino;
(i) dialkylamino;
(j) heteroalkyl;
(k) optionally substituted heterocycle;
(l) optionally substituted heterocyclylalkyl;
(m) optionally substituted heterocyclylalkoxy;
(n) alkylsulfonyl;
(o) aminosulfonyl, mono-alkylaminosulfonyl or di-alkylaminosulfonyl;
(p) heteroalkoxy; and
(q) carboxy;
—$NHSO_2R^6$ where $R^6$ is alkyl, heteroalkyl or optionally substituted heterocyclylalkyl;
(r) —$NHSO_2NR^7R^8$ where $R^7$ and $R^8$ are, independently of each other, hydrogen, alkyl or heteroalkyl;
(s) —Y-(alkylene)$_{n1}$—$R^9$ where: Y is a single bond, —O—, —NH— or —S(O)$_n$— (where n and n1 are each independently an integer from 0 to 2); and $R^9$ is halo, cyano, optionally substituted aryl, optionally substituted aralkyl, optionally substituted heteroaryl, optionally substituted heterocyclyl, —COOH, —$COR^{10}$, —$COOR^{11}$, —$CONR^{12}R^{13}$, —$SO_2R^{14}$, —$SO_2NR^{15}R^{16}$, —$NHSO_2R^{17}$ or —$NHSO_2NR^{18}R^{19}$, where $R^{10}$ is alkyl or optionally substituted heterocycle, $R^{11}$ is alkyl, and $R^{12}$, $R^{13}$, $R^{14}$, $R^{15}$, $R^{16}$, $R^{17}$, $R^{18}$ and $R^{19}$ are, independently of each other, hydrogen, alkyl or heteroalkyl;
(t) —C(=$NR^{20}$)($NR^{21}R^{22}$) where $R^{20}$, $R^{21}$ and $R^{22}$ independently represent hydrogen, alkyl or hydroxy, or $R^{20}$ and $R^{21}$ together are —$(CH_2)_n$— where n is 2 or 3 and $R^{22}$ is hydrogen or alkyl;
(u) —NHC(X)$NR^{23}R^{24}$ where X is —O— or —S—, and $R^{23}$ and $R^{24}$ are, independently of each other, hydrogen, alkyl or heteroalkyl;
(v) —$CONR^{25}R^{26}$ where $R^{25}$ and $R^{26}$ independently represent hydrogen, alkyl, heteroalkyl or optionally substituted heterocyclylalkyl, or $R^{25}$ and $R^{26}$ together with the nitrogen to which they are attached form an optionally substituted heterocyclyl ring;
(w) —S(O)$_n R^{27}$ where n is an integer from 0 to 2, and $R^{27}$ is alkyl, heteroalkyl, optionally substituted heterocyclylalkyl or —$NR^{28}R^{29}$ where $R^{28}$ and $R^{29}$ are, independently of each other, hydrogen, alkyl or heteroalkyl;
(x) cycloalkylalkyl, cycloalkylalkynyl and cycloalkylalkynyl, all optionally substituted with alkyl, halo, hydroxy or amino;
(y) arylaminoalkylene or heteroarylaminoalkylene;
(z) Z-alkylene-$NR^{30}R^{31}$ or Z-alkylene-$OR^{32}$ where Z is —NH—, —N(lower alkyl)- or —O—, and $R^{30}$, $R^{31}$ and $R^{32}$ are independently of each other, hydrogen, alkyl or heteroalkyl;
(aa) —OC(O)-alkylene-$CO_2H$ or —OC(O)—NR'R" where R' and R" are independently hydrogen or alkyl;
(bb) heteroarylalkenylene or heteroarylalkynylene;
(cc) hydrogen;
(dd) halo;
(ee) pseudohalo;
(ff) hydroxy;
(gg) optionally substituted alkoxy;
(hh) C(L)$R^{40}$, where L is O, S or $NR^{55}$; $R^{40}$ is hydrogen, optionally substituted alkyl, optionally substituted alkenyl, optionally substituted alkynyl, optionally substituted aryl, optionally substituted heteroaryl, optionally substituted heteroarylium, optionally substituted cycloalkyl, optionally substituted heterocyclyl, C(L)$R^{56}$, halo pseudohalo, $OR^{55}$, $SR^{55}$, $NR^{57}R^{58}$ or $SiR^{52}R^{53}R^{54}$; where $R^{52}$, $R^{53}$ and $R^{54}$ are selected as in (i) or (ii) as follows (i) $R^{52}$, $R^{53}$ and $R^{54}$ are each independently hydrogen, alkyl, alkenyl, alkynyl, aryl, heteroaryl, heteroarylium, cycloalkyl, heterocyclyl, $OR^{55}$ or $NR^{62}R^{63}$; or (ii) any two of $R^{52}$, $R^{53}$ and $R^{54}$ together form alkylene, alkenylene, alkynylene, heteroalkylene; and the other is selected as in (i); $R^{55}$ is hydrogen, alkyl, alkenyl, alkynyl, aryl, heteroaryl, heteroarylium, cycloalkyl or heterocyclyl; $R^{56}$ is hydrogen, alkyl, alkenyl, alkynyl, aryl, heteroaryl, heteroarylium, cycloalkyl, heterocyclyl, $OR^{55}$ or $NR^{64}R^{65}$; where $R^{64}$ and $R^{65}$ are each independently hydrogen, alkyl, alkenyl, alkynyl, aryl, heteroaryl, heteroarylium, cycloalkyl, heterocyclyl, $OR^{66}$ or $NR^{62}R^{63}$, or $R^{64}$ and $R^{65}$ together form alkylene, alkenylene, alkynylene, heteroalkylene, where $R^{66}$ is hydrogen, alkyl, alkenyl, alkynyl, aryl, heteroaryl, heteroarylium, cycloalkyl or heterocyclyl; $R^{57}$ and $R^{58}$ are selected as in (i) or (ii) as follows (i) $R^{57}$ and $R^{58}$ are each independently hydrogen, optionally substituted alkyl, alkenyl, alkynyl, aryl, heteroaryl, heteroarylium, cycloalkyl, heterocyclyl, $OR^{55}$, $NR^{67}R^{68}$ or C(L)$R^{69}$, where $R^{67}$ and $R^{68}$ are each independently hydrogen, alkyl, alkenyl, alkynyl, aryl, heteroaryl, heteroarylium, cycloalkyl or heterocyclyl, or together form alkylene, alkenylene, alkynylene, heteroalkylene; and $R^{69}$ is hydrogen, alkyl, alkenyl, alkynyl, aryl, heteroaryl, heteroarylium, cycloalkyl, heterocyclyl, $OR^{70}$ or $NR^{62}R^{63}$, where $R^{70}$ is alkyl, alkenyl, alkynyl, aryl, heteroaryl, heteroarylium, cycloalkyl, heterocyclyl; or (ii) $R^{57}$ and $R^{58}$ together form alkylene, alkenylene, alkynylene, heteroalkylene, or alkylenoxyalkylene; $R^{62}$ and $R^{63}$ are each independently hydrogen, alkyl, alkenyl, alkynyl, aryl, heteroaryl, heteroarylium, cycloalkyl, heterocyclyl, or $R^{62}$ and $R^{63}$ together form alkylene, alkenylene, alkynylene, heteroalkylene; and
(ii) optionally substituted alkyl; and
$R^6$ is selected from the group consisting of:
(a) hydrogen;
(b) halo;
(c) alkyl; and
(d) alkoxy.

In certain embodiments, the compound is selected with a proviso that when $R^2$ is alkyl, then G is not a saturated heterocyclic group with one nitrogen.

In certain embodiments, $R^1$ is hydrogen or alkyl. In certain embodiments, $R^1$ is hydrogen or methyl.

In certain embodiments, $R^2$ is hydrogen or alkyl. In certain embodiments, $R^2$ is hydrogen.

In certain embodiments, G is aryl. In other embodiments, G is phenyl.

In certain embodiments, $R^3$ is heterocyclyl, amino, —Y—$R^9$, —NHC(X)$NR^{23}R^{24}$, —$CONR^{25}R^{26}$, $COR^{40}$, where $R^{40}$ is hydrogen, optionally substituted alkyl, optionally substituted aryl, optionally substituted heteroaryl, optionally substituted cycloalkyl, optionally substituted heterocyclyl, C(L)$R^{56}$, $OR^{55}$ or $NR^{57}R^{58}$.

In certain embodiments, $R^9$ is optionally substituted aryl, optionally substituted heteroaryl, optionally substituted heterocyclyl, —COOH, —$COR^{10}$, —$COOR^{11}$, —$CONR^{12}R^{13}$, where $R^{10}$ is alkyl or optionally substituted heterocycle, $R^{11}$ is alkyl, and $R^{12}$ and $R^{13}$ are, independently of each other, hydrogen, alkyl or heteroalkyl.

In certain embodiments, where $R^{40}$ is hydrogen, optionally substituted alkyl, optionally substituted aryl, optionally substituted heteroaryl, optionally substituted cycloalkyl, optionally substituted heterocyclyl, $COR^{56}$, $OR^{55}$ or $NR^{57}R^{58}$.

In certain embodiments, $R^{55}$ is hydrogen, alkyl, aryl, heteroaryl, cycloalkyl, or heterocyclyl.

In certain embodiments, $R^{56}$ is hydrogen, alkyl, alkenyl, alkynyl, aryl, heteroaryl, heteroarylium, cycloalkyl, heterocyclyl, $OR^{55}$ or $NR^{64}R^{65}$; where $R^{64}$ and $R^{65}$ are each independently hydrogen or alkyl.

In certain embodiments, $R^{57}$ and $R^{58}$ are selected as in (i) or (ii) as follows (i) $R^{57}$ and $R^{58}$ are each independently hydrogen, optionally substituted alkyl, alkenyl, alkynyl, aryl, heteroaryl, heteroarylium, cycloalkyl, heterocyclyl, $OR^{55}$, $R^{67}R^{68}$ or $C(L)R^{69}$, where $R^{67}$, $R^{67}$ and $R^{68}$ are each independently hydrogen or alkyl, or (ii) $R^{57}$ and $R^{58}$ together form alkylene, alkenylene, alkynylene, heteroalkylene, or alkylenoxyalkylene.

In other embodiments, $R^3$ is halo, alkyl, amino, alkylamino, carboxy, alkylaminocarbonyl, cycloalkylaminocarbonyl, aralkylaminocarbonyl, heterocyclylcarbonyl, aminocarbonyl, alkoxycarbonyl, alkoxycarbonylamino, arylaminocarbonyl, oxazolyl, heterocyclyl and alkylaminocarbonylamino.

In other embodiments, $R^3$ is chloro, methyl, amino, carboxy, ethylaminocarbonyl, isopropylaminocarbonyl, cyclopropylaminocarbonyl, benzylaminocarbonyl, morpholinocarbonyl, aminocarbonyl, methoxycarbonyl, ethoxycarbonyl, ethoxycarbonylamino, isopropyloxycarbonylamino, isobutyloxycarbonylamino, phenylaminocarbonyl, oxazolyl, triazinyl and ethylaminocarbonylamino.

In certain embodiments, $R^4$ is alkyl or alkoxy. In certain embodiments, $R^4$ is methyl or methoxy. In other embodiments, $R^4$ is methyl.

In certain embodiments, $R^5$ is hydrogen, alkyl, alkoxycarbonyl, aralkylaminocarbonyl, alkylaminocarbonyl and cycloalkylaminocarbonyl.

In certain embodiments, $R^5$ is hydrogen, ethoxycarbonyl, benzylaminocarbonyl, methylaminocarbonyl and cyclopropylaminocarbonyl.

In certain embodiments, $R^6$ is hydrogen.

In certain embodiments, the compounds provided herein have formula:

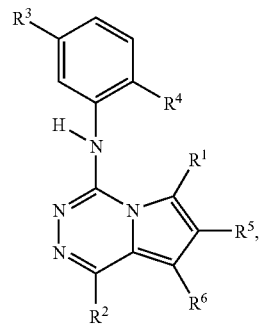

wherein $R^3$ is chloro, methyl, amino, carboxy, ethylaminocarbonyl, isopropylaminocarbonyl, cyclopropylaminocarbonyl, benzylaminocarbonyl, morpholinocarbonyl, aminocarbonyl, methoxycarbonyl, ethoxycarbonyl, ethoxycarbonylamino, isopropyloxycarbonylamino, isobutyloxycarbonylamino, phenylaminocarbonyl, oxazolyl, triazinyl, or ethylaminocarbonylamino; and the other variables are as described elsewhere herein.

In certain embodiments, the compounds provided herein have formula:

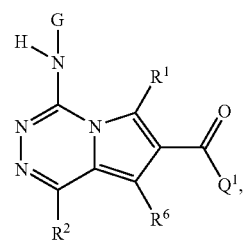

wherein the variables are as described elsewhere herein.

In certain embodiments, the compounds provided herein have formula:

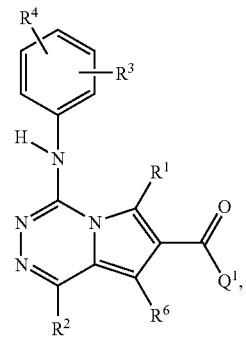

wherein $Q^1$ is alkyl, alkoxy, aralkylamino, alkylamino and cycloalkylamino and the other variables are as described elsewhere herein.

In certain embodiments, the compounds provided herein have formula:

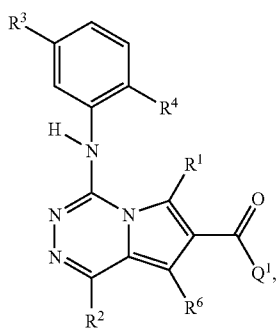

the other variables are as described elsewhere herein.

In certain embodiments, the compounds provided herein have formula:

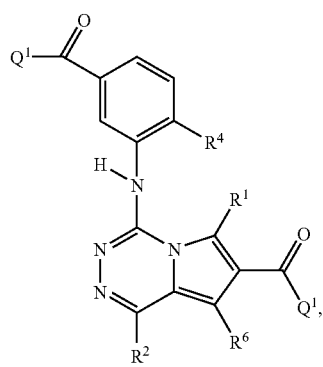

the other variables are as described elsewhere herein.

In certain embodiments, the compounds provided herein have formula:

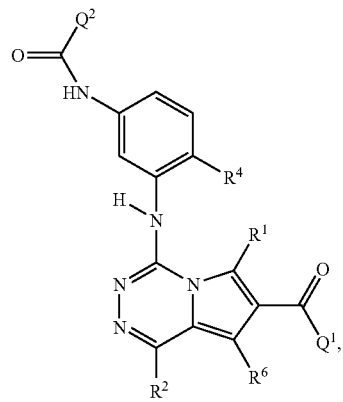

wherein $Q^2$ is alkoxy, or alkylaminocarbonyl and the other variables are as described elsewhere herein.

In certain embodiments, the compounds provided herein have formula:

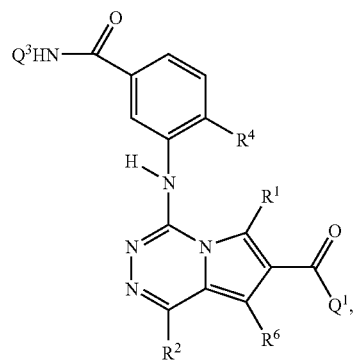

wherein $Q^3$ is hydrogen, alkyl, cycloalkyl, aralkyl and aryl; and the other variables are as described elsewhere herein.

In certain embodiments, the compound provided is selected from:

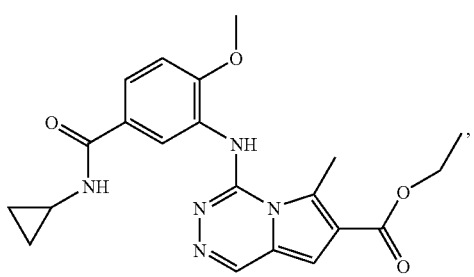

1.

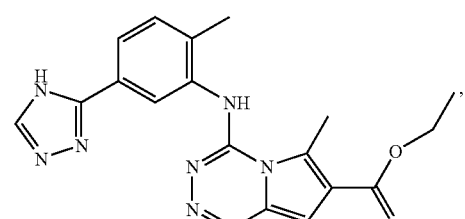

2.

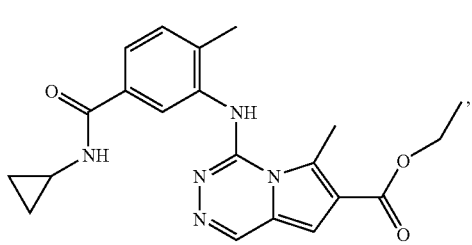

3.

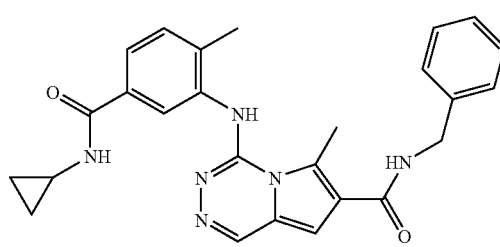

4.

-continued

-continued
18.
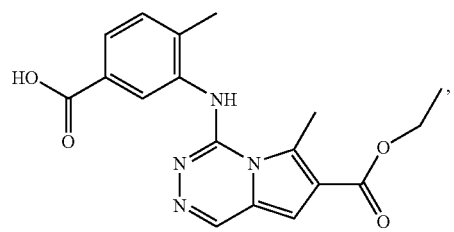
19.
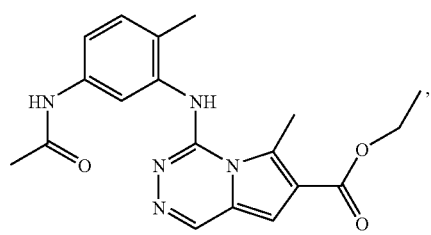
20.
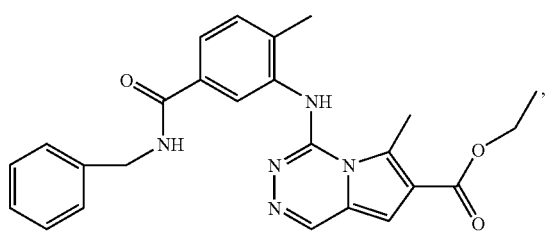
21.
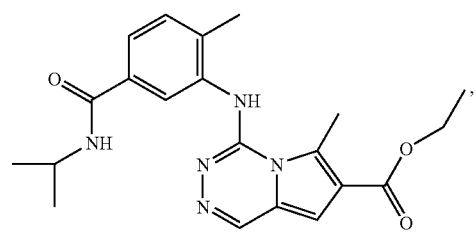
22.
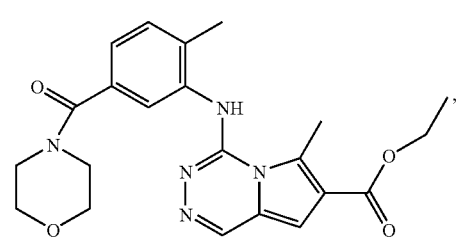
23.
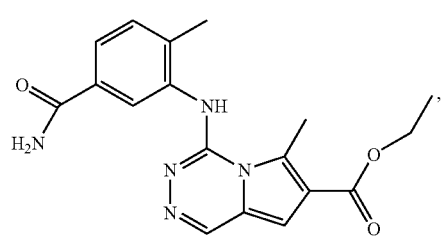
-continued
24.
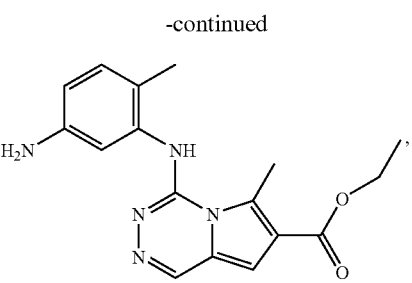
25.
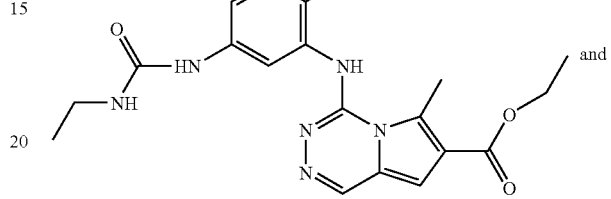
and
26.
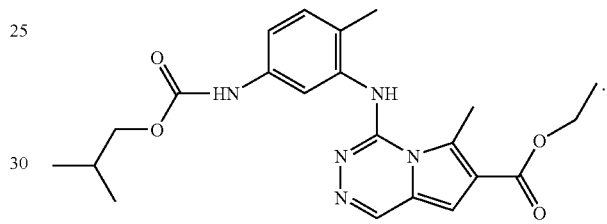
In certain embodiments, the compound provided is selected from:

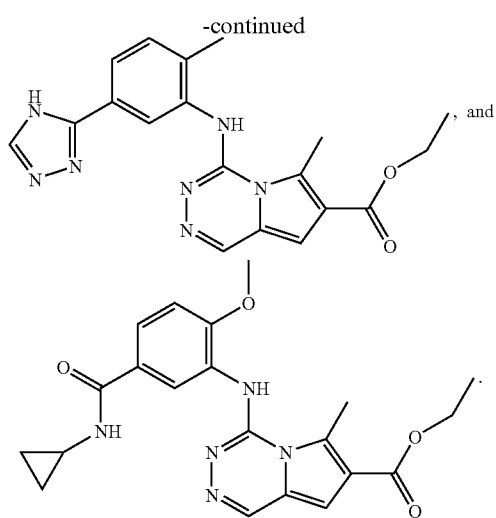

C. Preparation of the Compounds

Compounds provided herein can be prepared according to the following schemes and the knowledge of one skilled in the art. An exemplary method useful for the preparation of compounds provided herein is illustrated in scheme 1.

Appropriately substituted pyrrolo[1,2-d][1,2,4]triazin-4-ylamines of type (I), provided herein, can be made by several means, for example as shown in scheme 1, reaction of an appropriately substituted amine with a reagent such as 1,1'thiocarbonyldi-2(1H)-pyridone, 1,1'-thiocarbonyldiimidazole or thiophosgene in a solvent such as methylene chloride or dioxane yields the isothiocyanate. Treatment of the isothiocyanate with an appropriately substituted (1H-pyrrol-2-ylmethylene)-hydrazine yields the thiourea which is methylated and cyclized at elevated temperature to give compound I.

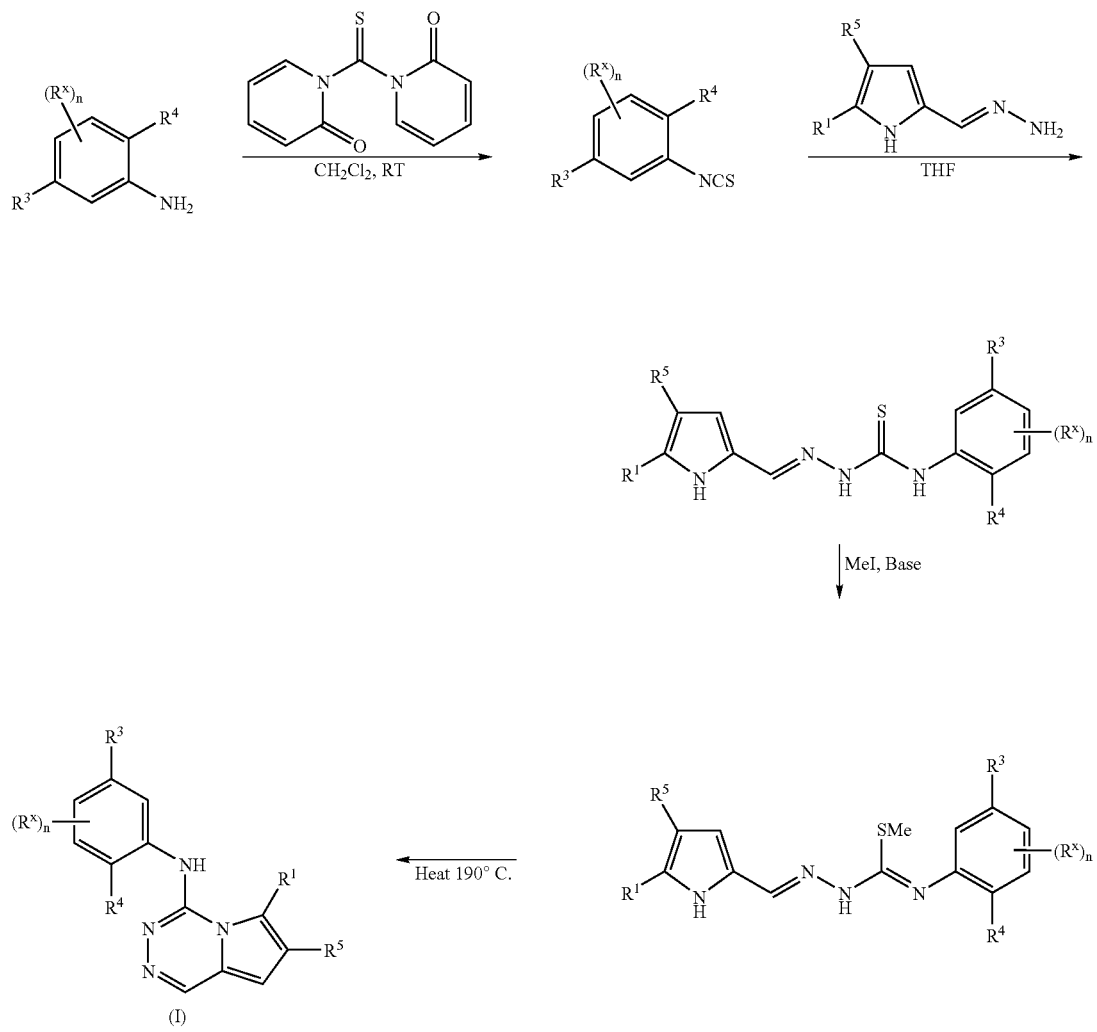

References of additional synthetic methods are as follows:
1) Heterocycle formation reactions: Bioorg. Med. Chem. Letters 12: 3125-3128 (2002)

Preparation of various thioisocyanates, from the corresponding aniline can be readily accomplished via the following procedure. The aniline is treated with 1,1'-thiocarbonyldi-2(1H)-pyridone in $CH_2Cl_2$ for 1-10 hrs. Typically, a precipitate forms, which is collected by filtration to give the product. Alternatively, the solvent is removed in vacuo and the resulting material purified by the many methods known to those skilled in art. Also, the preparation described in Example 1A provides another useful means of thioisocyanate preparation.

D. Formulation of Pharmaceutical Compositions

The pharmaceutical compositions provided herein contain therapeutically effective amounts of one or more of compounds provided herein that are useful in the prevention, treatment, or amelioration of one or more of the symptoms of p38-kinase-associated and/or JNK-associated conditions, including TNF-α, IL-1, and/or IL-8 mediated conditions. Such conditions include, but are not limited to, inflammatory diseases, autoimmune diseases, destructive bone disorders, proliferative disorders, angiogenic disorders, infectious diseases, neurodegenerative diseases, and viral diseases.

In certain embodiments, the disease is selected from pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, SARS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin induced platelet aggregation, endotoxemia and/or toxic shock syndrome, and conditions associated with prostaglandin endoperoxidase synthase-2.

In addition, p38 and/or JNK inhibitors provided herein inhibit the expression of inducible pro-inflammatory proteins such as prostaglandin endoperoxide synthase-2 (PGHS-2), also referred to as cyclooxygenase-2 (COX-2). Accordingly, additional p38 and/or JNK-associated conditions include edema, analgesia, fever and pain, such as neuromuscular pain, headache, pain caused by cancer, dental pain and arthritis pain. The compounds provided herein also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus. When the terms "p38-associated condition"; "p38-associated disease or disorder"; "JNK-associated condition" or "JNK-associated disease or disorder" are used herein, each is intended to encompass all of the conditions identified above as if repeated at length, as well as any other condition that is affected by p38 kinase and/or JNK activity.

The compositions contain one or more compounds provided herein. The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel *Introduction to Pharmaceutical Dosage Forms, Fourth Edition* 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of conditions associated with p-38 kinase and/or JNK, including TNF-α, IL-1, and/or IL-8 mediated conditions. Such conditions include, but are not limited to, cancer, coronary restenosis, osteoporosis and syndromes characterized by chronic inflammation and/or autoimmunity.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with p-38 kinase and/or JNK, including TNF-α, IL-1, and/or IL-8 mediated conditions, as described herein.

Typically a therapeutically effective dosage should produce a serum concentration of active ingredient of from about 0.1 ng/ml to about 50-100 μg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and in one embodiment, from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing diseases or disorders associated with p-38 associated conditions and/or JNk associated conditions including, but not limited to, inflammatory diseases, autoimmune diseases, destructive bone disorders, proliferative disorders, angiogenic disorders, infectious diseases, neurodegenerative diseases, and viral diseases as described herein. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. In one embodiment, modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, polyethylene glycol, glycerine, propylene glycol, domethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), dimethylacetamide, using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active Compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, in certain embodiments, 0.1-85%, typically 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as diseases or disorders associated with p-38 kinase and or JNK including, but not limited to, inflammatory diseases, autoimmune diseases, destructive bone disorders, proliferative disorders, angiogenic disorders, infectious diseases, neurodegenerative diseases, and viral diseases. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603 Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylenevinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, in certain embodiments, more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, in one embodiment, 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, in one embodiment, 5-35 mg, in other embodiment, about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044, 126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, in one embodiment, less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

E. Evaluation of the Activity of the Compounds

Standard physiological, pharmacological and biochemical procedures are available for testing the compounds to identify those that possess biological activities that modulate the activity of cytokines, including the p38 kinase and/or JNK activity.

Compound inhibitory activity was measured in a radioactive enzyme assay. The buffer composition was adopted from Lisnock et al (Biochemistry, 1998, vol. 37, pp 16573-16581). Peptide substrate was selected from Chen et al (Biochemistry, 2000, vol. 39, 2079-2087). The concentrations of p38α, [γ-$^{33}$P-ATP] and peptide were equal 1 nM, 85 uM and 250 uM, respectively. Incorporation of $^{33}$P into peptide was measured using absorption on filtermats with subsequent wash with 100 mM phosphoric acid followed by ethanol.

Other conditions for the p38α enzymatic assay were also described in literature. They either differed from the assay described in either buffer composition (Biochemistry, 2000, vol. 39, 2079-2087)), or substrate (Biochemistry, 1998, vol. 37, pp 16573-16581), or both (Protein Sci., 1998, vol. 7, pp. 2249-2255).

F. Methods of Use of the Compounds and Compositions

In a further embodiment, the compounds provided herein can be used in the treatment, prevention, or amelioration of one or more symptoms of inflammatory diseases. A compound provided herein can be used, in another embodiment, for the manufacture of a medicament for the treatment or prophylaxis of inflammatory diseases.

The compounds provided herein are selective inhibitors of p38 kinase activity, in particular, isoforms p38α and p38β and/or JNK activity, in particular, JNK1, JNK2 and JNK3 activity. Accordingly, compounds provided herein are useful for treating conditions associated with p38 kinase and/or JNK activity. Such conditions include diseases in which cytokine levels are modulated as a consequence of intracellular signaling via p38, and in particular, diseases that are associated with an overproduction of cytokines IL-1, IL-4, IL-8, and TNF-α. The diseases that may be treated or prevented by the p38 inhibitors provided herein, may also be conveniently grouped by the cytokine (IL-1, TNF, IL-6, IL-8) that is believed to be responsible for the disease.

Thus, an IL-1-mediated disease or condition includes rheumatoid arthritis, osteoarthritis, stroke, endotoxemia and/or toxic shock syndrome, inflammatory reaction induced by endotoxin, inflammatory bowel disease, tuberculosis, atherosclerosis, muscle degeneration, cachexia, psoriatic arthritis, Reiter's syndrome, gout, traumatic arthritis, rubella arthritis, acute synovitis, diabetes, pancreatic .beta.-cell disease and Alzheimer's disease.

TNF-mediated disease or condition includes, rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections, such as HIV, CMV, influenza and herpes; and vetinary viral infections, such as lentivirus infections, including, but not limited to equine infectious anemia virus, caprine arthritis virus, visna virus or maedi virus; or retrovirus infections, including feline immunodeficiency virus, bovine immunodeficiency virus, or canine immunodeficiency virus.

IL-8 mediated disease or condition includes diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, the compounds provided herein may be used topically to treat or prevent conditions caused or exacerbated by IL-1 or TNF. Such conditions include inflamed joints, eczema, psoriasis, inflammatory skin conditions such as sunburn, inflammatory eye conditions such as conjunctivitis, pyresis, pain and other conditions associated with inflammation.

Provided herein are methods of treating a disease by administering a compound provided herein that inhibits p38 kinase and/or JNK activity. Also provided herein are methods for inhibiting or delaying the onset of a disease or disorder by administering a compound provided herein. Methods provided herein can be used to achieve a full or partial reduction of the symptoms of a disease or disease state, and/or to alleviate, ameliorate, or lessen, the disease or disorder and/or its symptoms. When reference is made herein to inhibition of "p-38α/βkinase," this means that either p38α and/or p38β kinase are inhibited. Thus, reference to an $IC_{50}$ value for inhibiting p-38α/β kinase means that the compound has such effectiveness for inhibiting at least one of, or both of, p38α and p38β kinases. When reference is made herein to inhibition of "JNK 1/2/3," this means that either JNK1 and/or JNK2 or JNK3 are inhibited. Thus, reference to an IC50 value for inhibiting JNK 1/2/3 means that the compound has such effectiveness for inhibiting at least one, two, or three of c-Jun N-terminal kinases.

In view of their activity as inhibitors of p38α/β kinase and/or JNK activity, compounds provided herein are useful in treating p-38 and/or JNK-associated conditions including, but not limited to, inflammatory diseases, autoimmune diseases, destructive bone disorders, proliferative disorders, angiogenic disorders, infectious diseases, neurodegenerative diseases, and viral diseases.

In one embodiment, the specific conditions or diseases that may be treated with the compounds provided herein include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, SARS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin induced platelet aggregation, endotoxemia and/or toxic shock syndrome, and conditions associated with prostaglandin endoperoxidase synthase-2.

In addition, p38 and/or JNK inhibitors provided herein inhibit the expression of inducible pro-inflammatory proteins such as prostaglandin endoperoxide synthase-2 (PGHS-2), also referred to as cyclooxygenase-2 (COX-2). Accordingly, additional p38 and/or JNK-associated conditions include edema, analgesia, fever and pain, such as neuromuscular pain, headache, pain caused by cancer, dental pain and arthritis pain. The compounds provided herein also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

G. Combination Therapy

Also provided herein are methods treating p38 kinase and/or JNK-associated conditions by administering to a subject in need thereof an effective amount of compounds provided herein alone or in combination with each other and/or other suitable therapeutic agents useful in treating such conditions. Exemplary of such other therapeutic agents include corticosteroids, rolipram, calphostin, CSAIDs, 4-substituted imidazo (1,2-A)quinoxalines as disclosed in U.S. Pat. No. 4,200,750 and in S. Ceccarelli et al, "Imidazo (1,2-a)quinoxalin-4-amines: A Novel Class of Nonxanthine $A_1$ Adenosine Receptor Antagonists," *European Journal of Medicinal Chemistry* Vol. 33, (1998), at pp. 943-955; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathioprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds provided herein, may be used, for example, in those amounts indicated in the Physicians' Desk Reference (PDR) or as otherwise determined by one of ordinary skill in the art. In the methods provided herein, such other therapeutic agent(s) may be administered prior to, simultaneously with, or following the administration of the compounds provided herein.

The following Examples illustrate embodiments herein, and are not intended to limit the scope of the claims. Abbreviations employed in the Examples are defined below. Compounds of the Examples are identified by the example and step in which they are prepared (for example, "1A" denotes the title compound of step A of Example 1), or by the example only where the compound is the title compound of the example (for example, "2" denotes the title compound of Example 2).

ABBREVIATIONS

Ph=phenyl
Bz=benzyl
t-Bu=tertiary butyl
Me=methyl
Et=ethyl
Pr=propyl
Iso-P or i-Pr=isopropyl
MeOH=methanol
EtOH=ethanol
EtOAc=ethyl acetate
Boc=tert-butyloxycarbonyl
CBZ=carbobenzyloxy or carbobenzoxy or benzyloxycarbonyl
DCM or $CH_2Cl_2$=dichloromethane
DCE=1,2-dichloroethane
DMF=dimethyl formamide
DMSO=dimethyl sulfoxide
TFA=trifluoroacetic acid
THF=tetrahydrofuran
HATU=O-(7-Azabenzotriazol-1-yl-N,N,N',N'-tetramethyluronium hexafluorophosphate
KOH=potassium hydroxide
$K_2CO_3$=potassium carbonate
$POCl_3$=phosphorous oxychloride
KOtBu=potassium t-butoxide EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
NaH=sodium hydride
NaOH=sodium hydroxide
$Na_2S_2O_3$=sodium thiosulfate
$Na_2SO_4$=sodium sulfate
Pd=palladium
Pd/C=palladium on carbon
min=minute(s)
L=liter
mL=milliliter
µL=microliter
g=gram(s)
mg=milligram(s)
mol=moles
mmol=millimole(s)
meq=milliequivalent
RT or rt=room temperature
ret. t. or $t_R$=HPLC retention time (minutes)
sat or sat'd=saturated

EXAMPLES

Mass spectra were obtained 4 on an HP 1100 mass spectrometer. In the examples: "HPLC (condition A)" refers to evaluation of the material by HPLC using a Thermal C18 column of 3 mm in diameter; a seven minute linear gradient with solvents from 5% A to 95% A (residual is B) over the seven minutes. Solvent A is acetonitrile with 0.325% TFA and solvent B is water with 0.325% TFA. $t_R$ is the retention time observed for the compound.

Example 1

Preparation of 4-(5-Cyclopropylcarbamoyl-2-methoxy-phenylamino)-6-methyl-pyrrolo[1,2-d][1,2,4]triazine-7-carboxylic acid ethyl ester

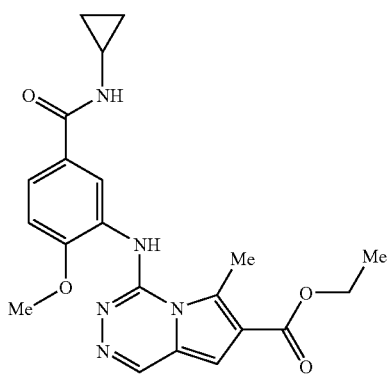

A. 3-Isothiocyanato-4-methoxy-benzoic acid

To a solution of 4-methoxy-benzoic acid (1.20 g, 7.18 mmol), 30 mL of water with sufficient conc. HCL to dissolve, was added $CSCl_2$ (0.55 mL, 7.18 mmol). The reaction was stirred for 2.5 hrs at room temperature. The resulting white solid was collected by filtration and washed with water and dried in vacuo to give the title compound, 1.37 g as a white solid. This material was used without further purification.

B. 5-Hydrazonomethyl-2-methyl-1H-pyrrole-3-carboxylic acid ethyl ester

To a solution of 5-formyl-2-methyl-1H-pyrrole-3-carboxylic acid ethyl ester (6.30 g, 0.034 mol) in EtOH (6.3 mL) was added a solution of hydrazine (1.69 mL, 0.034 mol). The reaction mixture was stirred at RT overnight. The resulting precipitate was filtered and dried in vacuo to give the titled compound, 6.79 g as a light yellow solid. This material was used without further purification.

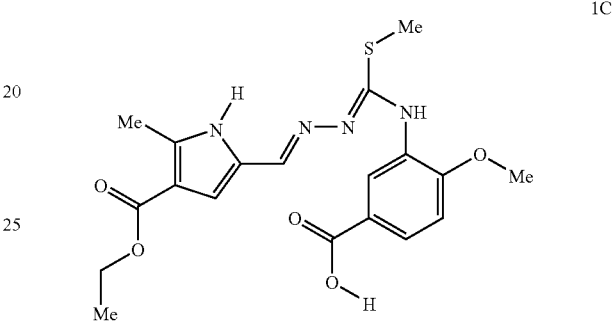

C. The Preparation of 1C

To anhydrous THF (1.0 mL) was added 1A (32 mg, 0.153 mmol) and 1B (100 mg, 0.154 mmol) and stirred at RT for 1.5 h. To this reaction was added sat'd $NaHCO_3$ (0.2 mL) and MeI (29 µL, 0.47 mmol). The reaction was then stirred overnight, filtered through a Celite pad, and the solvents removed in vacuo. The resulting product was purified by silica gel chromatography (MeOH 1-4%; $CH_2Cl_2$) to give 1C compound (31 mgs).

D. 4-(5-Carboxy-2-methoxy-phenylamino)-6-methyl-pyrrolo[1,2-d][1,2,4]triazine-7-carboxylic acid ethyl ester A solution of 3B (31 mg, 0.074 mmol) in DMF (0.5 mL) was heated by microwave radiation to 190° C. for 30 minutes. The reaction was again heated for 30 minutes under the same conditions and water (1 mL) was added. The precipitate was collected by filtration. The filtrate was extracted with $CH_2CL_2$ (1×1 mL). The extracts were combined and dried over $MgSO_4$, filtered and the solvent removed in vacuo. The precipitate was combined with the extract and purified by silica gel chromatography (4-7% MeOH in $CH_2Cl_2$). The solvent was removed in vacuo to yield the title compound (13 mg) as an orange solid.

E. 4-(5-Cyclopropylcarbamoyl-2-methoxy-phenylamino)-6-methyl-pyrrolo[1,2-d][1,2,4]triazine-7-carboxylic acid ethyl ester To a suspension of HOBt (30 mg, 0.20 mmol), EDCI (30 mg, 0.16 mmol), cyclopropyl amine (20 uL, 0.29 mmol) in DMF (0.5 mL) at RT was added 4-(5-carboxy-2-methoxy-phenylamino)-6-methyl-pyrrolo[1,2-d][1,2,4]triazine-7-carboxylic acid ethyl ester (13 mg, 0.035 mmol). The reaction was stirred overnight. Water (1 mL) was added and the precipitate collected. The product was purified by flash chromatography on silica gel (1-3% MeOH in $CH_2Cl_2$) giving the title compound, 7 mg, as a yellowish solid. HPLC (condition A) $t_R$ 4.37 min. MS m/z 410 [M+H]$^+$.

Example 2

Preparation of 4-[2-Methyl-5-(4H-[1,2,4]triazol-3-yl)-phenylamino]-6-methyl-pyrrolo[1,2-d][1,2,4]triazine-7-carboxylic acid ethyl ester

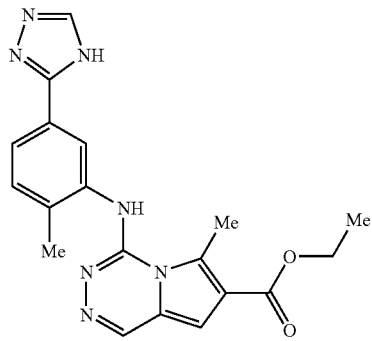

A. The Preparation of 2A 3-(3-Isothiocyanato-4-methyl-phenyl)-4H-[1,2,4]triazole (22 mg, 0.10 mmol) and 1B (20 mg, 0.10 mmol) in THF (1.0 mL) were stirred at RT for 1 h. To this reaction mixture was added sat'd $NaHCO_3$ (0.2 mL) and MeI (28 mg). The reaction mixture was stirred for 2 h. Water (5 mL) was added and the mixture was extracted with EtOAc (2×20 mL). The combined extracts were washed with brine and dried over $MgSO_4$. The product was purified by silica gel chromatography to give 2A, 35 mg.

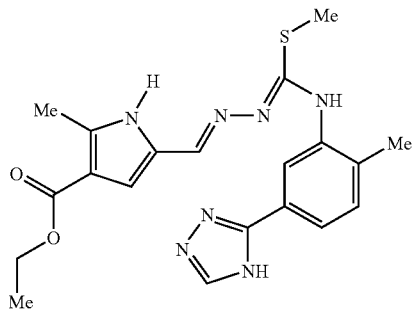

2A

B. 4-[2-Methyl-5-(4H-[1,2,4]triazol-3-yl)-phenylamino]-6-methyl-pyrrolo[1,2-d][1,2,4]triazine-7-carboxylic acid ethyl ester 2A (20 mg, 0.047 mmol) in DMF (0.5 mL) was heated by microwave radiation to 190° C. for 30 minutes. The resulting material was purified by preparative HPLC to give the titled compound, 12 mg. HPLC (condition A) $t_R$ 4.48 min. MS m/z 378 [M+H]$^+$.

Example 3

Preparation of 4-(5-Cyclopropylcarbamoyl-2-methyl-phenylamino)-6-methyl-pyrrolo[1,2-d][1,2,4]triazine-7-carboxylic acid ethyl ester

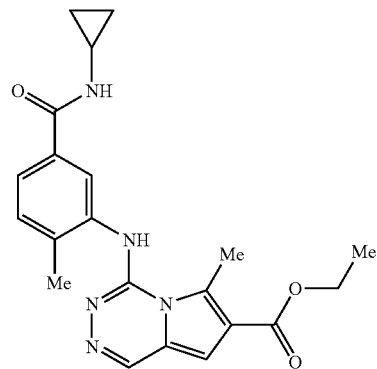

A. Preparation of 3A

N-Cyclopropyl-3-isothiocyanato-4-methyl-benzamide (159 mg, 0.69 mmol) and 1B (134 mg, 0.0.69 mmol) in THF (1.0 mL) were stirred at RT overnight. The solvent was removed by evaporation giving a yellow solid. This material was suspended in THF (5 mL) and NaOH (0.2 N, 5 mL). To this reaction was added MeI (43 µL, 0.69 mmol) and stirred at rt for 30 min. Water (5 mL) was added and the mixture was extracted with $CH_2Cl_2$ (2×20 mL). The combined extracts were dried over $Na_2SO_4$ and the solvent removed in vacuo, to yield 3A, (311 mg). This material was used without further purification.

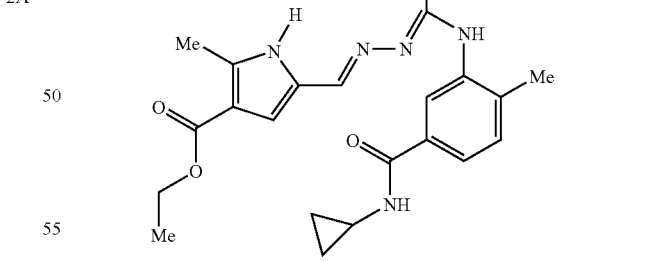

3A

B. 4-(5-Cyclopropylcarbamoyl-2-methyl-phenylamino)-6-methyl-pyrrolo[1,2-d][1,2,4]triazine-7-carboxylic acid ethyl ester 3A (0.69 mmol) in HOAc (4 mL) was heated by microwave radiation to 190° C. for 15 minutes. The resulting material was purified by preparative HPLC to give the titled compound, 55 mg. HPLC (condition A) $t_R$ 4.91 min. MS m/z 394 [M+H]$^+$.

Example 4

Preparation of 4-(5-Cyclopropylcarbamoyl-2-methyl-phenylamino)-6-methyl-pyrrolo[1,2-d][1,2,4]triazine-7-carboxylic acid benzylamide

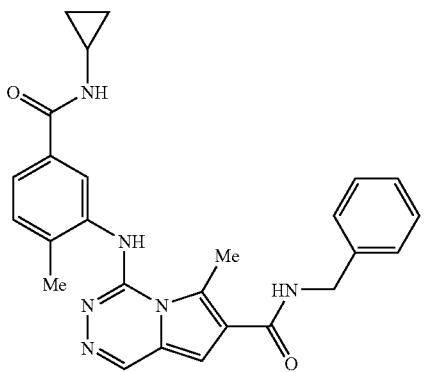

A. 4-(5-Cyclopropylcarbamoyl-2-methyl-phenylamino)-6-methyl-pyrrolo[1,2-d][1,2,4]triazine-7-carboxylic acid benzylamide To a solution of 4-(5-cyclopropylcarbamoyl-2-methyl-phenylamino)-6-methyl-pyrrolo[1,2-d][1,2,4]triazine-7-carboxylic acid (37, 0.13 mmol) in DMF (1 mL) was added EDCI (37 mg, 0.20 mmol), HOBt (30 mg, 0.20 mmol), Et$_3$N (45 µL) and benzylamine (29 µl, 0.27 mmol). The reaction mixture was stirred for 3 h at rt. The crude material was purified by preparative HPLC to give the titled product, 3.3 mg as an off white solid. HPLC (condition A) t$_R$ 4.40 min. MS m/z 455 [M+H]$^+$.

Example 5

Preparation of 4-(5-Ethoxycarbonylamino-2-methyl-phenylamino)-6-methyl-pyrrolo[1,2-d][1,2,4]triazine-7-carboxylic acid ethyl ester

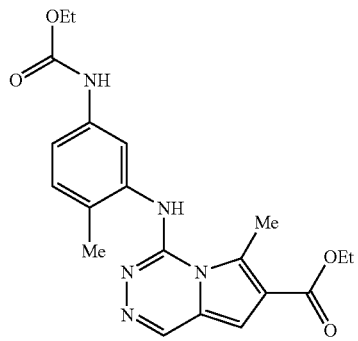

A. The Preparation of 5A

To anhy. THF (2.0 mL) was added (3-isothiocyanato-4-methyl-phenyl)-carbamic acid ethyl ester (32 mg, 0.153 mmol) and 1B (250 mg, 1.28 mmol) and stirred at RT for 2 h. To this reaction was added sat'd NaHCO$_3$ (0.5 mL) and MeI (120 µL, 1.93 mmol). The reaction was then stirred overnight, filtered through a Celite pad, and the solvents removed in vacuo. The resulting product was purified by silica gel chromatography (1/1 EtOAc/hexanes) to give 5C (280 mg) as a yellow solid.

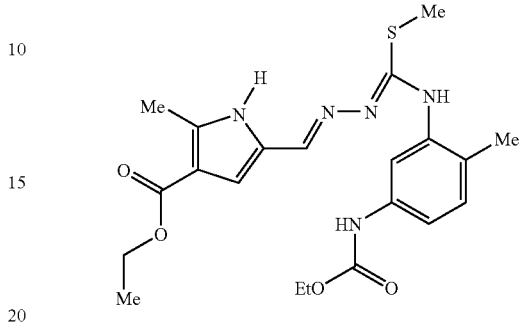

B. 4-(5-Ethoxycarbonylamino-2-methyl-phenylamino)-6-methyl-pyrrolo[1,2-d][1,2,4]triazine-7-carboxylic acid ethyl ester 5A (50 mg) in DMF (0.2 mL) was heated by microwave radiation to 190° C. for 30 minutes. The resulting material was purified by preparative HPLC to give the titled compound, 15 mg. HPLC (condition A) t$_R$ 5.54 min. MS m/z 398 [M+H]$^+$.

Example 6

JNK Enzymatic Assay

In a final reaction volume of 20 µL, 5 nM human recombinant Jnk2 was incubated in the absence or presence of putative JNK inhibitors in increasing concentrations with 25 mM HEPES pH 7.5, 20 mM p-glycerophosphate, 10 mM MgCl$_2$, 0.1 mM sodium orthovanadate, 0.005% Tween® 80, 10 uM [γ-$^{33}$P-ATP], 500 µM IPTTPITTTYFFFKKK peptide substrate and 2 mM DTT. The reaction was initiated by the addition of the [g-$^{33}$P-ATP]. After incubation for 20 minutes at 30° C., the aliquots were transferred onto P30/GF filtermats (PerkinElmer). Each filtermat washed four times in 100 ml 0.5% phosphoric acid, 0.5 mM pyrophosphate, then twice in 50 ml ethanol, dried and sealed into bag containing 5 ml of OptiPhase "SuperMix" liquid scintillation cocktail (PerkinElmer). Radioactivity incorporated into peptide was quantified on Trilux 1450 Microbeta plate-reader. IC$_{50}$ values were calculated using SigmaPlot.

p38α Assay

The p38α assay employed is based on measurement of ADP released in the reaction of interest through NADH oxidation obtained by coupling with pyruvate kinase and lactate dehydrogenase reactions. The assays were performed in 384-well UV-plates. The final volume was 25 uL prepared from the addition of 2.5 uL compound dissolved in 10% DMSO, 17.5 uL of assay buffer and 5 uL of ATP. Assay buffer contains the following reagents to give final concentration in the assay: 25 mM HEPES, 20 mM 2-glycerophosphate, pH 7.6, 10 mM MgCl$_2$, 0.1 mM sodium orthovanadate, 0.5 mM phosphoenolpyruvate, 0.12 mM NADH, 3.1 mg/ml LDH, 6.67 mg/ml pyruvate kinase, 0.25 mM peptide substrate, 2 mM DTT, 0.005% Tween 80 and 20 nM p38α kinase from Upstate. Test compounds are preincubated with p38α kinase for 60 min and the reaction started by addition of ATP to 0.15 mM final concentration. Reaction rates were measured at 340 nm using SpectraMax plate-reading spectrophotometer for 10 min at 37° C. Inhibition data were analyzed by non-linear least-squares regression using SigmaPlot.

Results

The compounds exemplified herein showed activity in the above assays as inhibitors of p38 kinase. In addition, these compounds have been shown to inhibit JNK2. Most of the compounds exhibited p38α kinase and JNK2 kinase $IC_{50}$ values of less than 10 μM, many less than 1 μM. The p38 inhibitory and JNK2 inhibitory activities of certain compounds provided herein are shown below in Table 1. For p38 kinase and JNK2 kinase $IC_{50}$ values, "+++" represents <1 μM, "++" represents between 1.0 and 10 μM and "+" represents >10 μM.

TABLE 1

| Compound | p38α inhibition | JNK |
|---|---|---|
| 1 | ++ | ++ |
| 2 | ++ | NA |
| 3 | +++ | +++ |
| 4 | +++ | +++ |
| 5 | +++ | +++ |
| 6 | ++ | ++ |
| 7 | +++ | +++ |
| 8 | +++ | ++ |
| 9 | ++ | ++ |
| 10 | NA | ++ |
| 11 | ++ | ++ |
| 12 | ++ | ++ |
| 13 | NA | ++ |
| 14 | ++ | ++ |
| 15 | ++ | ++ |
| 16 | ++ | ++ |
| 17 | N/A | ++ |
| 18 | ++ | ++ |
| 19 | + | ++ |
| 20 | ++ | ++ |
| 21 | NA | + |
| 22 | NA | + |
| 23 | NA | + |
| 24 | + | + |

The invention claimed is:

1. A compound, or a pharmaceutically-acceptable acid addition salt thereof, wherein the compound has the formula (V):

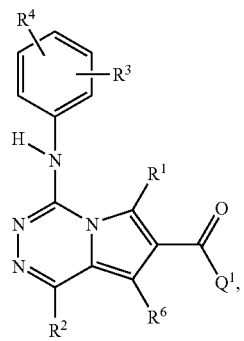

(V)

where
$R^1$ is hydrogen, alkyl or halo;
$R^2$ is hydrogen or alkyl;

$R^3$ is chloro, methyl, amino, carboxy, ethylaminocarbonyl, isopropylaminocarbonyl, cyclopropylaminocarbonyl, benzylaminocarbonyl, morpholinocarbonyl, aminocarbonyl, methoxycarbonyl, ethoxycarbonyl, ethoxycarbonylamino, isopropyloxycarbonylamino, isobutyloxycarbonylamino, phenylaminocarbonyl, oxazolyl, triazinyl or ethylaminocarbonylamino;

$R^4$ is selected from the group consisting of hydrogen, halo, alkyl, alkoxy and hydroxy;

$R^6$ is selected from the group consisting of hydrogen, halo, alkyl and alkoxy; and $Q^1$ is alkyl, alkoxy, aralkylamino, alkylamino or cycloalkylamino;

wherein

"alkyl" means a straight- or branched-chain unsubstituted hydrocarbon group of 1-to-20 carbon atoms;

"alkoxy" means a radical —OR, where R is alkyl, as defined above;

"halo" means fluoro, chloro, bromo or iodo;

"cycloalkyl" means a saturated or partially-unsaturated nonaromatic cyclic hydrocarbon ring system containing 1-to-3 rings with 3-to-7 carbons per ring, which may be further fused with an unsaturated $C_3$-$C_7$-carbocyclic ring; and "aryl" means a monovalent monocyclic or bicyclic aromatic hydrocarbon radical of 6-to-10 ring atoms, where the aryl ring may optionally be fused to a 5-, 6- or 7-membered monocyclic saturated ring optionally containing 1 or 2 heteroatoms independently selected from oxygen, nitrogen and sulfur, with the remaining ring atoms being carbons, wherein one or two carbon atoms may be optionally replaced by a carbonyl group.

2. The compound according to claim 1, or a pharmaceutically-acceptable acid addition salt thereof, wherein the compound has the formula (VI):

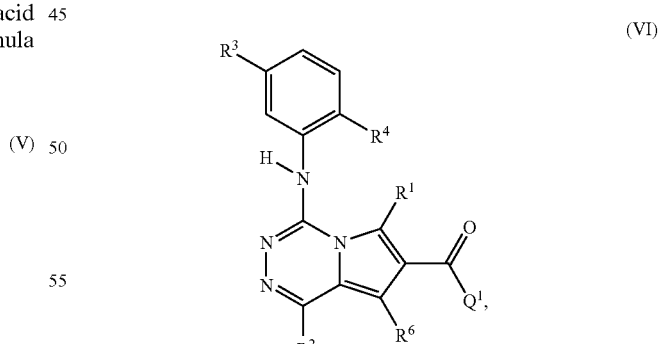

(VI)

where the variables and included terms are as defined in claim 5.

3. The compound according to claim 1, or a pharmaceutically-acceptable acid addition salt thereof, wherein the compound has the formula (VII):

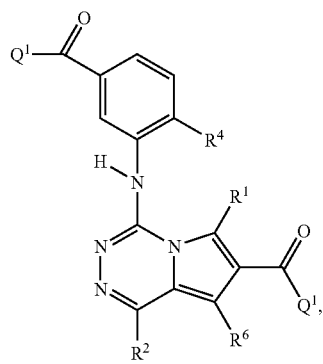

(VII)

where R³' is carboxy, ethylaminocarbonyl, isopropylaminocarbonyl, cyclopropylaminocarbonyl, benzylaminocarbonyl, morpholinocarbonyl, aminocarbonyl, methoxycarbonyl, ethoxycarbonyl or phenylaminocarbonyl, and the other variables and included terms are as defined in claim 1.

4. The compound according to claim 1, or a pharmaceutically-acceptable acid addition salt thereof, wherein the compound has the formula (VIII):

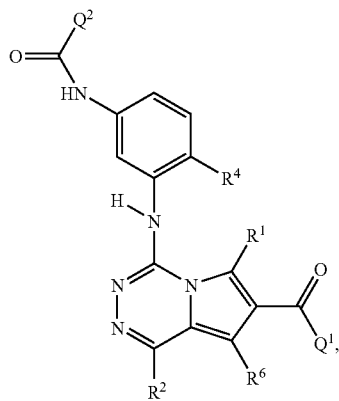

(VIII)

where Q²-C(=O)—NH— is ethoxycarbonylamino, isopropyloxycarbonylamino, isobutyloxycarbonylamno or ethylaminocarbonylamino and the other variables and included terms are as defined in claim 1.

5. The compound according to claim 1 selected from:

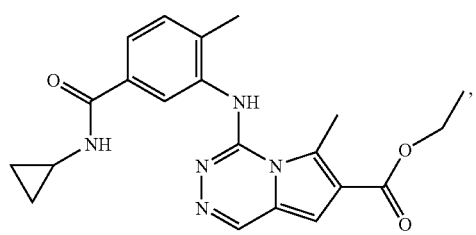

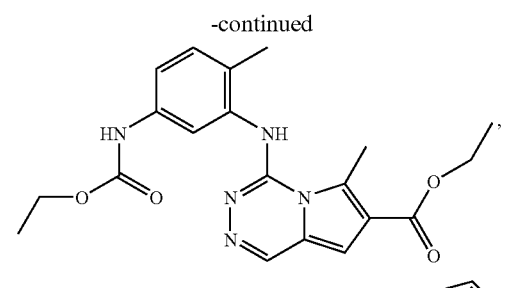

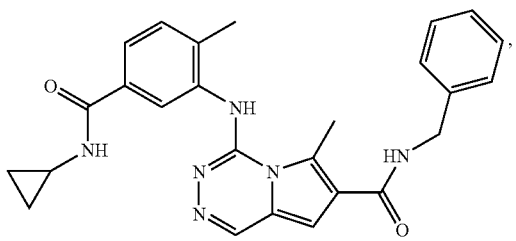

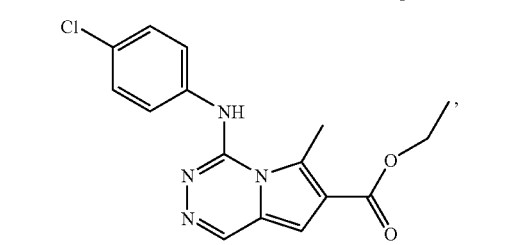

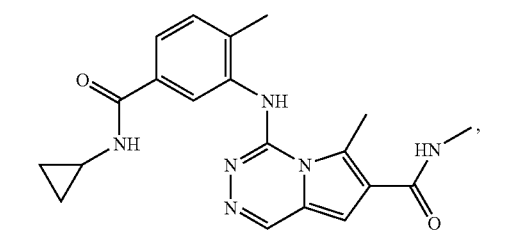

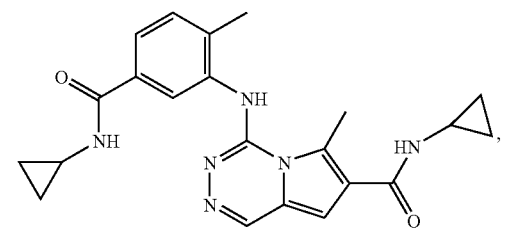

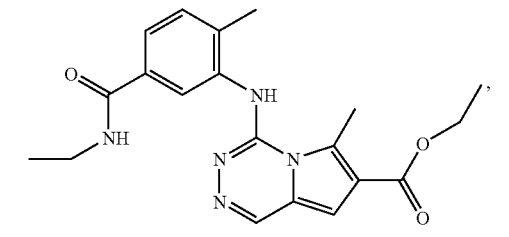

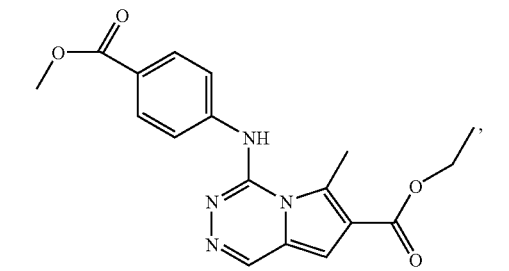

-continued
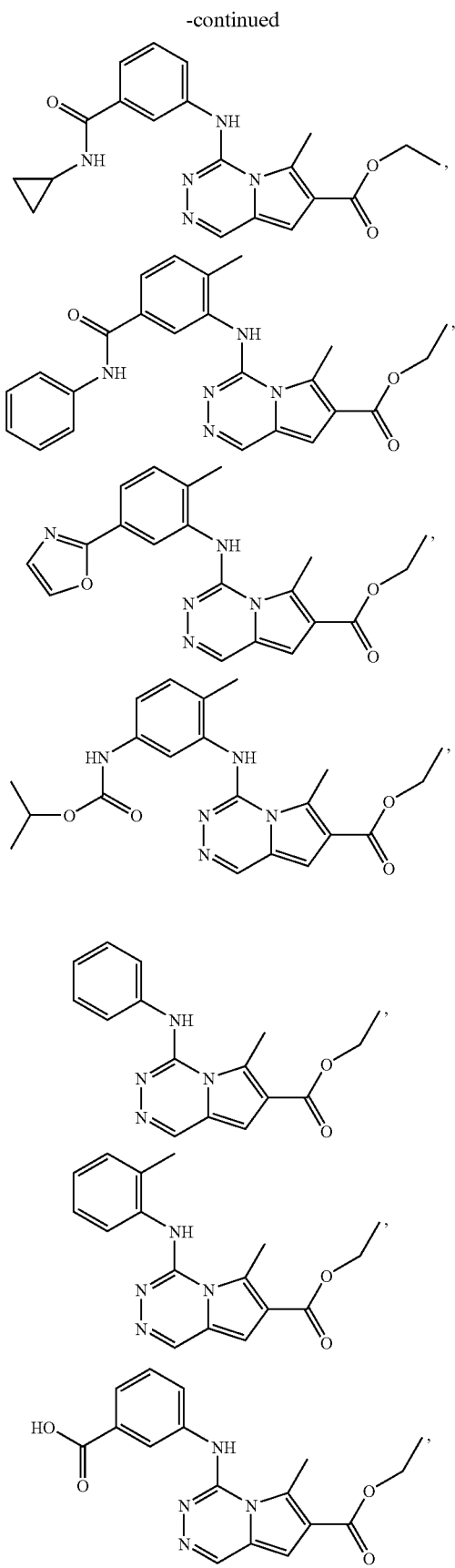
-continued
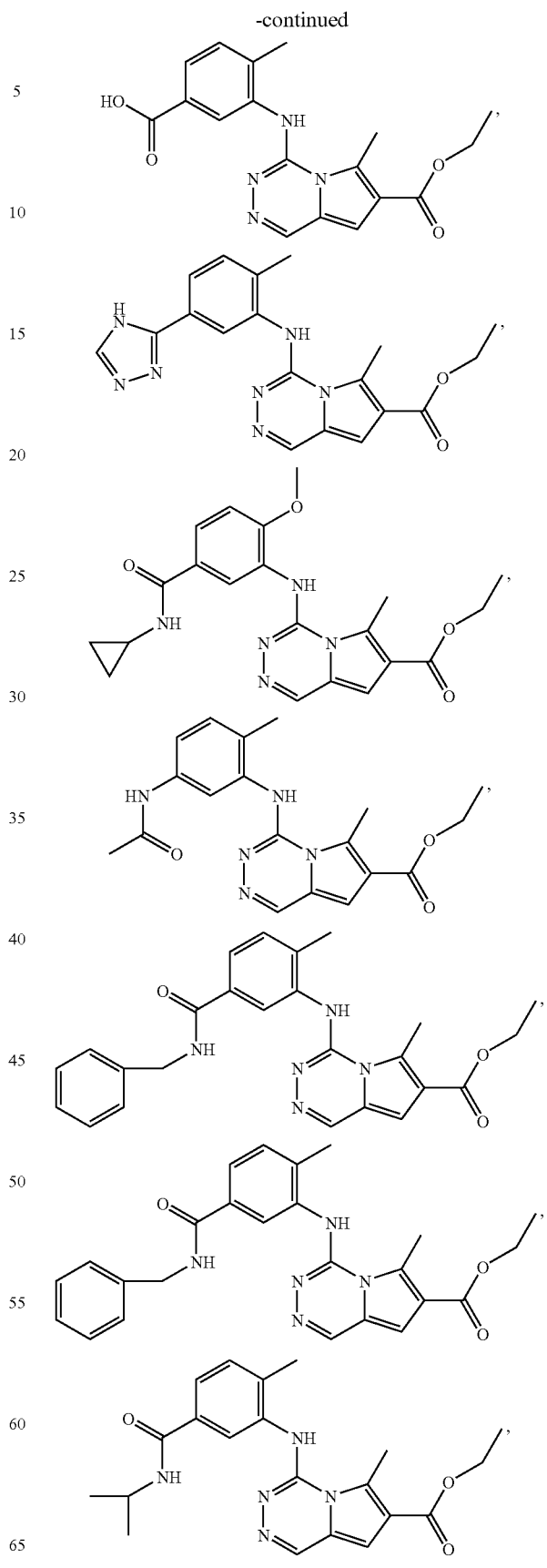

-continued

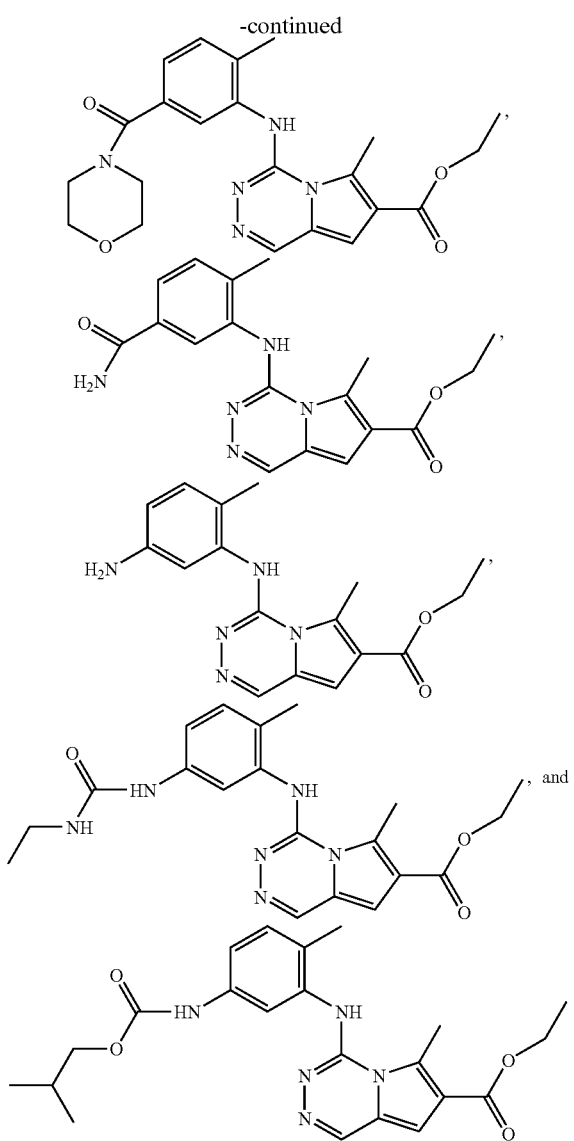

or a pharmaceutically-acceptable acid addition salt thereof.

6. A method of treating or ameliorating one or more symptoms of cyclokine-mediated diseases or disorders, selected from the group consisting of rheumatoid arthritis and inflammatory bowel disease, comprising administering to a subject in need thereof a therapeutically-effective amount of a compound of the formula (V):

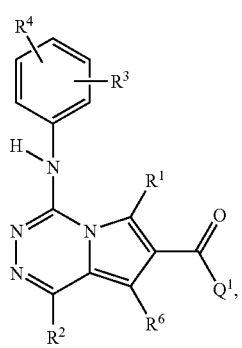

wherein
R$^1$ is hydrogen, alkyl or halo;
R$^2$ is hydrogen or alkyl;
R$^3$ is chloro, methyl, amino, carboxy, ethylaminocarbonyl, isopropylaminocarbonyl, cyclopropylaminocarbonyl, benzylaminocarbonyl, morpholinocarbonyl, aminocarbonyl, methoxycarbonyl, ethoxycarbonyl, ethoxycarbonylamino, isopropyloxycarbonylamino, isobutyloxycarbonylamino, phenylaminocarbonyl, oxazolyl, triazinyl or ethylaminocarbonylamino;
R$^4$ is selected from the group consisting of hydrogen, halo, alkyl, alkoxy and hydroxy;
R$^6$ is selected from the group consisting of hydrogen, halo, alkyl and alkoxy; and
Q$^1$ is alkyl, alkoxy, aralkylamino, alkylamino or cycloalkylamino, where
"alkyl" means a straight- or branched-chain unsubstituted hydrocarbon group of 1-to-20 carbon atoms;
"alkoxy" means a radical —OR, where R is alkyl, as defined above;
"halo" means fluoro, chloro, bromo or iodo;
"cycloalkyl" means a saturated or partially-unsaturated nonaromatic cyclic hydrocarbon ring system containing 1-to-3 rings with 3-to-7 carbons per ring, which may be further fused with an unsaturated C$_3$-C$_7$-carbocyclic ring; and
"aryl" means a monovalent monocyclic or bicyclic aromatic hydrocarbon radical of 6-to-10 ring atoms, where the aryl ring may optionally be fused to a 5-, 6- or 7-membered monocylic saturated ring optionally containing 1 or 2 heteroatoms independently selected from oxygen, nitrogen and sulfur, with the remaining ring atoms being carbons, wherein one or two carbon atoms may be optionally replaced by a carbonyl group.

7. The method of claim 6, further comprising administering a corticosteroid, a CSAID, a 4-substituted imidazo[1,2-A]quinoxaline, interleukin-10, a glucocorticoid, a salicylate, nitric oxide, an immunosuppressant, a nuclear translocation inhibitor, a non-steroidal anti-inflammatory drug, a steroid, an antiviral agent, an antiproliferative agent, a cytotoxic drug, a TNF-α inhibitor, a soluble TNF receptor, and/or rapamycin.

8. A pharmaceutical composition comprising a compound of the formula (V):

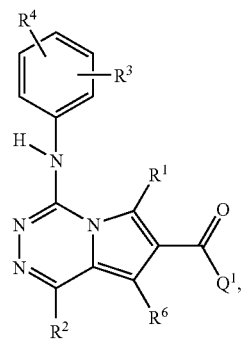

wherein
R$^1$ is hydrogen, alkyl or halo;
R$^2$ is hydrogen or alkyl;
R$^3$ is chloro, methyl, amino, carboxy, ethylaminocarbonyl, isopropylaminocarbonyl, cyclopropylaminocarbonyl, benzylaminocarbonyl, morpholinocarbonyl, aminocarbonyl, methoxycarbonyl, ethoxycarbonyl, ethoxycarbonylamino, isopropyloxycarbonylamino, isobutyloxycarbonylamino, phenylaminocarbonyl, oxazolyl, triazinyl or ethylaminocarbonylamino;

R⁴ is selected from the group consisting of hydrogen, halo, alkyl, alkoxy and hydroxy;

R⁶ is selected from the group consisting of hydrogen, halo, alkyl and alkoxy; and Q¹ is alkyl, alkoxy, aralkylamino, alkylamino or cycloalkylamino, where "alkyl" means a straight- or branched-chain unsubstituted hydrocarbon group of 1-to-20 carbon atoms;

"alkoxy" means a radical —OR, where R is alkyl, as defined above;

"halo" means fluoro, chloro, bromo or iodo;

"cycloalkyl" means a saturated or partially-unsaturated nonaromatic cyclic hydrocarbon ring system containing 1-to-3 rings with 3-to-7 carbons per ring, which may be further fused with an unsaturated $C_3$-$C_7$-carbocyclic ring; and "aryl" means a monovalent monocyclic or bicyclic aromatic hydrocarbon radical of 6-to-10 ring atoms, where the aryl ring may optionally be fused to a 5-, 6- or 7-membered monocylic saturated ring optionally containing 1 or 2 heteroatoms independently selected from oxygen, nitrogen and sulfur, with the remaining ring atoms being carbons, wherein one or two carbon atoms may be optionally replaced by a carbonyl group, or a pharmaceutically-acceptable acid addition salt thereof and a pharmaceutically-acceptable carrier therefor.

9. The pharmaceutical composition of claim 8, further comprising one or more of the following: a corticosteroid, rolipram, calphostin, a CSAID, a 4-substituted imidazo[1,2-A]quinoxaline, interleukin-10, a glucocorticoid, a salicylate, nitric oxide, an immunosuppressant, a nuclear translocation inhibitor, deoxyspergualin, ibuprofen, celecoxib, rofecoxib, prednisone, dexamethasone, abacavir, methotrexate, leflunomide, FK506, azathioprine, cyclophosphamide, tenidap, an anti-TNF antibody, a soluble TNF receptor, and rapamycin.

10. The compound according to claim 1, wherein "alkyl" means a straight- or branched-chain unsubstituted hydrocarbon group of 1-to-7 carbon atoms; and "halo" means fluoro or chloro.

11. A compound selected from

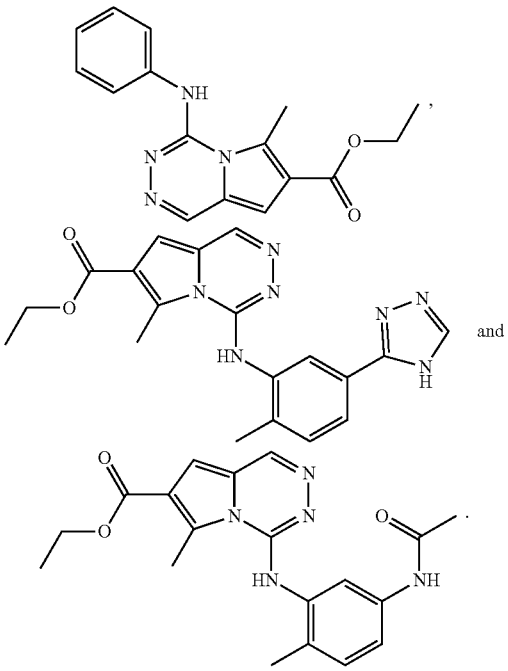

* * * * *